United States Patent
Son et al.

(10) Patent No.: US 11,224,873 B2
(45) Date of Patent: Jan. 18, 2022

(54) MICROFLUIDIC SYSTEM INCORPORATING LIGHT ABSORBING MATERIALS

(71) Applicant: Kryptos Biotechnologies, Inc., Hayward, CA (US)

(72) Inventors: Jun Ho Son, Albany, CA (US); Sewoon Han, Albany, CA (US); Jinyong Lee, Emeryville, CA (US)

(73) Assignee: Kryptos Biotechnologies, Inc., Hayward, CA (US)

( * ) Notice: Subject to any disclaimer, the term of this patent is extended or adjusted under 35 U.S.C. 154(b) by 340 days.

(21) Appl. No.: 16/353,926

(22) Filed: Mar. 14, 2019

(65) Prior Publication Data

US 2019/0283023 A1    Sep. 19, 2019

Related U.S. Application Data

(60) Provisional application No. 62/652,861, filed on Apr. 4, 2018, provisional application No. 62/643,494, filed on Mar. 15, 2018.

(51) Int. Cl.
| | |
|---|---|
| *B01L 3/00* | (2006.01) |
| *B01L 7/00* | (2006.01) |
| *B01L 9/00* | (2006.01) |

(52) U.S. Cl.
CPC ......... *B01L 3/502715* (2013.01); *B01L 3/567* (2013.01); *B01L 7/52* (2013.01);
(Continued)

(58) Field of Classification Search
CPC ...... B01L 3/502715; B01L 3/567; B01L 7/52; B01L 7/54; B01L 7/525; B01L 9/527;
(Continued)

(56) References Cited

U.S. PATENT DOCUMENTS 6,337,435 B1 * 1/2002 Chu .................. B01L 7/52
 136/203
9,132,398 B2 * 9/2015 Zhou ............... B01L 3/50273
(Continued)

FOREIGN PATENT DOCUMENTS

WO    2017019768 A1    2/2017
WO    2017127570 A1    7/2017

OTHER PUBLICATIONS

Siwei Lang, Quanbin Zhou, Xianhui Li, Ming Zhong and Hong Wang. "Electrical Properties of a Transparent Conductive ITO/Ga2O3/Ag/Ga2O3 Multilayer for Ultraviolet Light-Emitting Diodes". Nanomaterials (Basel). Mar. 2019; 9(3): 403 (Year: 2019).*

(Continued)

*Primary Examiner* — Michael L Hobbs
(74) *Attorney, Agent, or Firm* — Kilpatrick Townsend & Stockton LLP

(57) ABSTRACT

Systems and methods for light based heating of light absorbing sources for modification of nucleic acids through fast thermal cycling of polymerase chain reaction are provided. The system includes a polymeric fluidic device comprising one or more reaction wells. A first light absorbing material is disposed on a first support to define a reaction well and first and second ports are coupled to the reaction wells. The first and second ports are configured to allow input of a fluidic sample into the reaction well. A lyophilized reagent is pre-loaded in the reaction well. A light source is configured to illuminate the first light absorbing material. A first portion of light illuminated onto the first light absorbing material is absorbed into the first light absorbing material and is configured to elevate the temperature of the first light absorbing material to heat the fluidic sample within the reaction well.

23 Claims, 19 Drawing Sheets

(52) U.S. Cl.
CPC .............. *B01L 7/525* (2013.01); *B01L 7/54* (2013.01); *B01L 9/527* (2013.01); *B01L 2200/0689* (2013.01); *B01L 2200/10* (2013.01); *B01L 2300/044* (2013.01); *B01L 2300/0645* (2013.01); *B01L 2300/0663* (2013.01); *B01L 2300/0681* (2013.01); *B01L 2300/123* (2013.01); *B01L 2300/168* (2013.01); *B01L 2300/18* (2013.01); *B01L 2400/06* (2013.01)

(58) Field of Classification Search
CPC ......... B01L 2200/0689; B01L 2200/10; B01L 2200/0663; B01L 2200/23; B01L 2200/044; B01L 2200/18; B01L 2200/168; B01L 2200/0645; B01L 2200/1858; B01L 2400/06; C12Q 1/6844; C12Q 1/686
See application file for complete search history.

(56) References Cited

U.S. PATENT DOCUMENTS

| | | | |
|---|---|---|---|
| 2003/0008308 A1 | 1/2003 | Enzelberger et al. | |
| 2003/0190608 A1* | 10/2003 | Blackburn | B01L 7/525 435/6.11 |
| 2005/0009070 A1 | 1/2005 | Arciniegas et al. | |
| 2006/0068412 A1 | 3/2006 | Tang | |
| 2006/0068499 A1* | 3/2006 | Wohlstadter | G01N 33/585 436/172 |
| 2007/0292941 A1 | 12/2007 | Handique et al. | |
| 2008/0003649 A1* | 1/2008 | Maltezos | G01N 21/645 435/91.2 |
| 2015/0031039 A1 | 1/2015 | Pipper et al. | |
| 2016/0250640 A1 | 9/2016 | Williams et al. | |
| 2017/0113221 A1 | 4/2017 | Hoffman et al. | |
| 2017/0282184 A1 | 10/2017 | Ll et al. | |
| 2017/0327867 A1 | 11/2017 | Dohale et al. | |
| 2019/0283023 A1 | 9/2019 | Son et al. | |
| 2019/0283032 A1 | 9/2019 | Son et al. | |

OTHER PUBLICATIONS

International Search Report and Written Opinion for Application No. PCT/US 19/22331, dated Jul. 18, 2019, 12 pages.

Application PCT/US2019/022331, International Preliminary Report on Patentability, dated Sep. 24, 2020, 9 pages.

Invitation to Pay Additional Fees received in International Patent Application No. PCT/US2019/022331, dated May 13, 2019. 2 pages.

U.S. Appl. No. 16/353,907 , "Non-Final Office Action", dated Jun. 24, 2021, 9 pages.

EP19767655.4, "Partial Supplementary European Search Report", dated Nov. 15, 2021, 13 pages.

\* cited by examiner

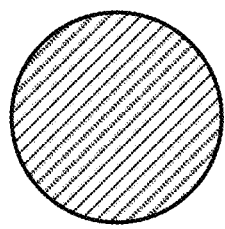
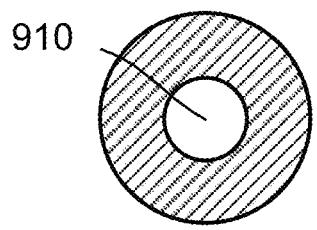
FIG. 9A  FIG. 9B
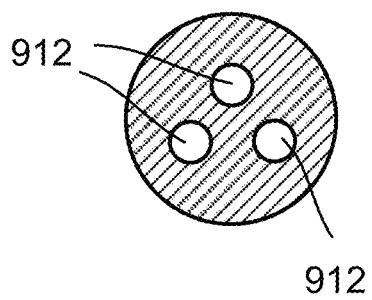
FIG. 9C

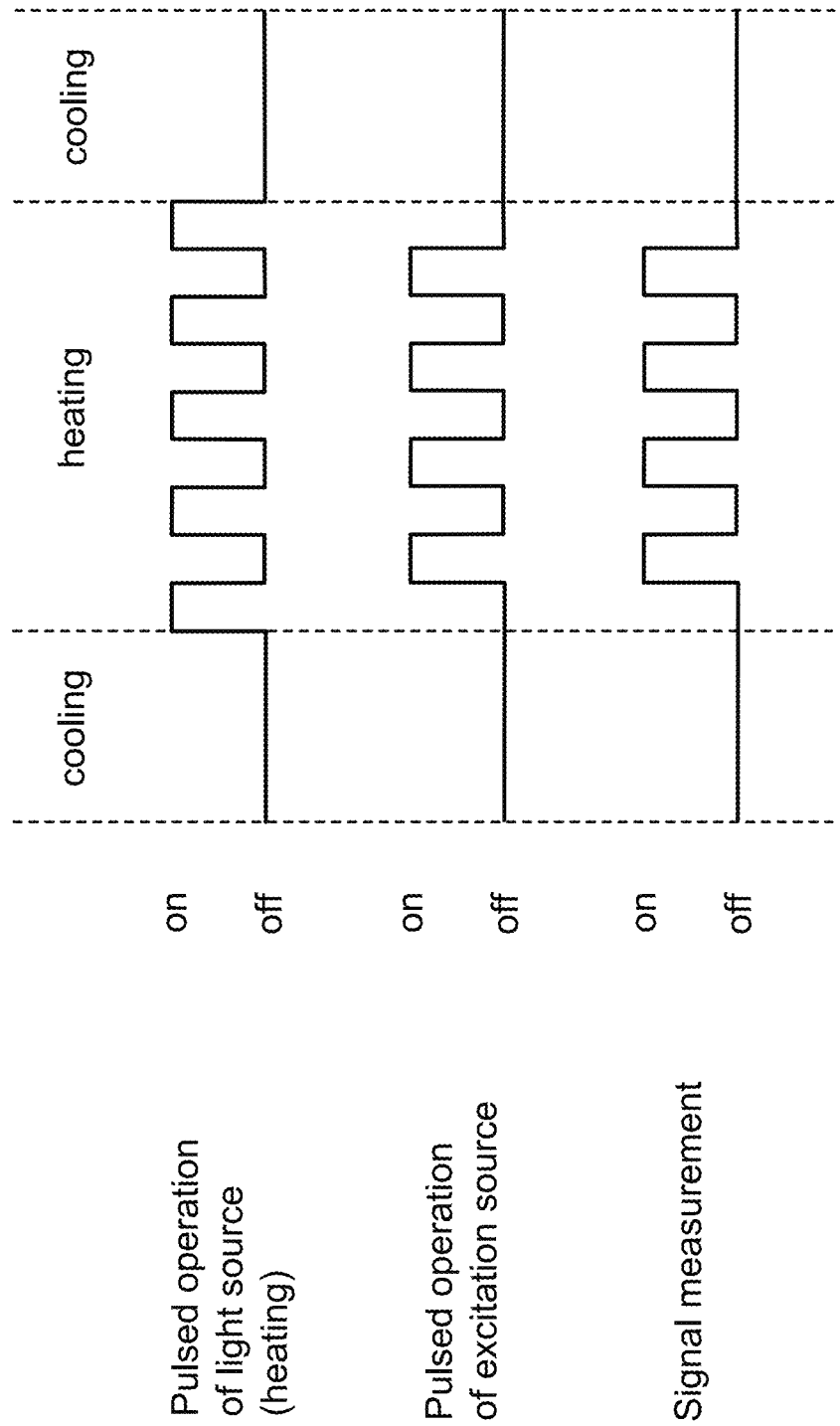

MICROFLUIDIC SYSTEM INCORPORATING LIGHT ABSORBING MATERIALS

CROSS-REFERENCES TO RELATED APPLICATIONS

This application claims priority to U.S. Provisional Patent Application No. 62/643,494, filed on Mar. 15, 2018, and U.S. Provisional Patent Application No. 62/652,861, filed on Apr. 4, 2018, the contents of both of which are hereby incorporated by reference in their entirety for all purposes.

The following regular U.S. patent applications (including this one) are being filed concurrently, and the entire disclosure of the other applications are incorporated by reference into this application for all purposes:

The following regular U.S. patent applications (including this one) are being filed concurrently, and the entire disclosure of the other applications are incorporated by reference into this application for all purposes:

Application No. 16/353,907, filed Mar. 14, 2019, entitled "Method and System for Performing Heat Assisted Biochemical Reactions";

Application No. 16/353,926, filed Mar. 14, 2019, entitled "Microfluidic System Incorporating Light Absorbing Materials".

BACKGROUND OF THE INVENTION

Polymerase chain reaction (PCR), is an important technique in the fields of clinical laboratories, environmental science, forensic science and agricultural science. There is a need for rapid and accurate diagnostics of nucleic acids. Fast/ultrafast PCR is desirable for applications such as time-sensitive diagnosis of diseases, genetic disorders, and laboratory experiments amongst other applications. Accordingly, an ultrafast PCR system would be desirable for laboratory testing, and point of care testing that is robust, simple, easy to use and characterized by low power consumption.

SUMMARY OF THE INVENTION

In some aspects, a system is provided. The system can be utilized for nucleic acid modification. The system may comprise a transparent block which may comprise one or more intrusions. The system may comprise a light absorbing material disposed within the one or more intrusions of the transparent block. Additionally, the system may comprise a reaction vessel removably positioned onto the intrusions of the transparent block. The system may comprise a light source. The light source may be configured to be directed at the intrusions of the transparent block such that light from the light source may generate heat within the light absorbing material subsequently heating the reaction vessel.

In some aspects, a system is provided. The system can be used for nucleic acid modification and may comprise a polymeric reaction vessel comprising one or more wells. The system may comprise a light absorbing material disposed within the one or more wells of the reaction vessel. The system may comprise a transparent block with intrusions to hold the reaction vessel. It may also comprise a light source. The light source may be configured to be directed at the wells of the transparent block such that light from the light source may generate heat within the light absorbing material and may heat the reaction vessel. The system may also comprise a sealing film disposed on the reaction vessel.

In some aspects, a system is provided. The system can be used for nucleic acid modification and may comprise a polymeric fluidic device comprising one or more reaction wells. The system may comprise a first light absorbing material disposed on a first support to define a reaction well and a second light absorbing material disposed on a second support opposite the first support. The first and second ports may be coupled to the reaction wells; wherein the first and second ports may be configured to allow input of a fluidic sample into the reaction well. A lyophilized reagent may be pre-loaded on the reaction well. The system may further comprise a light source configured to illuminate the first light absorbing material; wherein a first portion of light illuminated onto the first light absorbing material may be absorbed into the first light absorbing material and a second portion of the light illuminated onto the first light absorbing material may be transmitted through the first light absorbing material. The light transmitted through the first light absorbing material may illuminate the second light absorbing material; wherein at least a portion of the transmitted light illuminated onto the second light absorbing material may be absorbed into the second light absorbing material. The absorbed light into the first light absorbing material and second light absorbing material may be configured to uniformly elevate a temperature of the first light absorbing material and second light absorbing material which may lead to heating of the fluidic sample within the reaction wells.

In some embodiments, the system may further comprise a sealing film disposed on the reaction vessel.

In some embodiments, the transparent block material may comprise transparent polymer, Polydimethylsiloxane (PDMS), glass, polymethylmethacrylate (PMMA), cyclic olefin copolymer (COC) and/or quartz.

In some embodiments, the shape of intrusions of the transparent block may be conical, hemispherical, pyramidal, rectangular, cylindrical, truncated, or dome-shaped. In some embodiments, an additional channel is placed around one or more of the intrusions.

In some embodiments, the transparent block may comprise a fluid circulation channel. In some embodiments, air/water/liquid flows through the circulation channel.

In some embodiments, the light absorbing material may comprise metallic thin film, non-metallic thin film, graphite, graphene, carbon nanotube, and/or paint. In some embodiments, the metallic thin film may comprise a single or multi-layer metallic structure; the metallic structure comprising one or more metals may be selected from the group comprising of: gold (Au), silver (Ag), nickel (Ni), titanium (Ti), chromium (Cr), germanium (Ge), palladium (Pd), ruthenium (Ru), tungsten (W), iridium (Ir), or platinum (Pt).

In some embodiments, the reaction vessel may comprise wells. The shape of the wells in the reaction vessel may be the same as the shape of the intrusions in the transparent block.

In some embodiments, the thickness of the reaction vessel may be less than 1 mm.

In some embodiments, the light source may be a light-emitting diode (LED), laser diode (LD), tungsten lamp, fluorescent lamp, halogen lamp, mercury lamp, xenon lamp, metal halide lamp, or combination thereof.

In some embodiments, the reaction vessel may be a PCR tube, a PCR plate, or a PCR strip.

In some embodiments, the system may further comprise one or more light sources. The number of light sources may be equal to the number of intrusions in the transparent block.

In some embodiments, an emission wavelength of the light source may not overlap with an excitation wavelength of a fluorescent dye used for real-time detection of nucleic acids.

In some embodiments, the sealing film further may comprise a light absorbing layer. In some embodiments, the sealing film may be colored.

In some embodiments, the system may further comprise one or more temperature sensors configured to monitor the temperature.

In some embodiments, the system may further comprise one or more excitation LEDs configured for excitation of a fluorescent dye.

In some embodiments, the system may further comprise one or more optical filters for the excitation LED.

In some embodiments, the system may further comprise two or more excitation LEDs. Each of the excitation LEDs can have a different wavelength to excite two or more fluorescent dyes.

In some embodiments, a high refractive index material may be disposed outside of the transparent heat block for internal reflection of light from an excitation LED.

In some embodiments, the system may further comprise a CMOS sensor, CCD sensor, photodiode or spectrophotometer.

In some embodiments, the system may further comprise a first filter for emission of a fluorescent dye and a second filter for elimination of light from the light source.

In some embodiments, the second filter may be a Distributed Bragg reflector (DBR) with high reflectivity over the emission wavelength of the light source.

In some embodiments the system may further comprise an embedded lens to focus an emissive light from a fluorescent dye. In some embodiments, the system may further comprise a lens disposed between the light source and the transparent block. The lens may be configured to focus emissive light from a light source. Alternatively, the lens may be configured to focus emissive light from a fluorescent dye.

In some embodiments, the photodiode may be an IR sensitivity suppressed type.

In some embodiments, lyophilized PCR reagents may be pre-loaded in the reaction vessel.

In some embodiments, the sealing film may comprise a sealing plate with or without a light absorbing material on the surface of the plate.

In some embodiments, the system may further comprise a processor, the processor may be coupled to the light source and may be configured with instructions to heat the reaction vessel with the light source.

In some embodiments the system may further comprise a processor. The processor may be coupled to the circulation channel. The processor may be configured with instructions to cool the reaction vessel.

In some embodiments, the light source may be pulsed for the photothermal heating of the light absorbing material.

In some embodiments, a duty cycle of pulsed operation may be from 1% to 100%.

In some embodiments, the light source and the excitation source may be pulsed in an alternating manner.

In some embodiments, a signal for detection of nucleic acids modification may be detected during an off cycle of pulsed operation of the light source.

In some embodiments, the light absorbing material further may comprise a passivation layer to prevent PCR reaction inhibition within the thermal cycling chamber. In some embodiments, the passivation layer may comprise an oxide thin film or a thin polymeric layer.

In some embodiments, one or more intrusions in the wells may comprise 2-D or 3-D microstructures or nanostructures in the form of a pillar array, 1D or 2D grating, photonic crystal, or hemi-sphere.

In some embodiments, reagents may be lyophilized. The lyophilized reagent may comprise a primer set for PCR. In some embodiments, the lyophilized reagent may comprise PCR reagent and primer set. In some embodiments, the lyophilized regent further may comprise a stabilizing reagent.

In some embodiments, the stabilizing reagent may comprise paraffin wax or hydrogel.

In some embodiments, the system may further comprise a fluidic valve between wells. In some embodiments, the fluidic valve may be operated by an external controller. The system may further include a lens disposed between the light source and the polymeric fluidic device.

In some embodiments, the polymeric fluidic device includes a fluid circulation channel. As an example, air, water, and /or liquid can flow through the circulation channel.

In some embodiments, the system may comprise a sample preparation module. The sample preparation module may comprise multiple compartments, and a cartridge; and a microfluidic PCR device. The microfluidic PCR device may comprise photonic PCR wells.

In some embodiments, the sample preparation module may further comprise a lysis system for photo-thermal lysis of cells.

In some embodiments, the sample preparation module may comprise one or more filters in a chamber. In some embodiments, the sample preparation module may comprise a first filter and a second filter wherein the first and second filter have different pore sizes. In some embodiments, a first filter may be used to remove large debris, crystals and/or large cells from a sample.

In some embodiments, a second filter may trap cells of interest based on the size of cells. In some embodiments, nucleic acids may be extracted from the cells trapped on the second filter. In some embodiments, the second filter may comprise a layer of light absorbing material. In some embodiments, a chamber below the second filter may comprise a layer of light absorbing material.

In some embodiments, the sample preparation module may comprise compartments further comprising electrodes placed around the compartment to change the pH of the solution by applying voltage.

In some embodiments, the sample preparation module may comprise a waste chamber. In some embodiments, the waste chamber may comprise absorbing porous paper, fabric or sponges to prevent re-flux of fluid.

In some embodiments, the sample preparation module may further comprise a microfluidic device comprising cartridges with wells.

In some embodiments, wells in the cartridges may be pre-loaded with a primer and probe set for the detection of target nucleic acids.

In some embodiments, a well in the cartridges may comprise a set of primers and probes to detect one target nucleic acid.

In some embodiments, a well in the cartridge may comprise a set of primers and probes to detect multiple target nucleic acids.

In some embodiments, the system may comprise a light absorbing material, wherein the light absorbing material may comprise one or more open areas. In some embodiments, the open area may form 1% to 90% of the light absorbing material.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIGS. 9A-9C are schematics of different forms of light absorbing material, in accordance with some embodiments.

FIG. 11A is a schematic depiction of pulsed operation of the light source and the excitation source in conjunction with signal measurement, in accordance with some embodiments.

DETAILED DESCRIPTION OF SPECIFIC EMBODIMENTS

Figure 1:
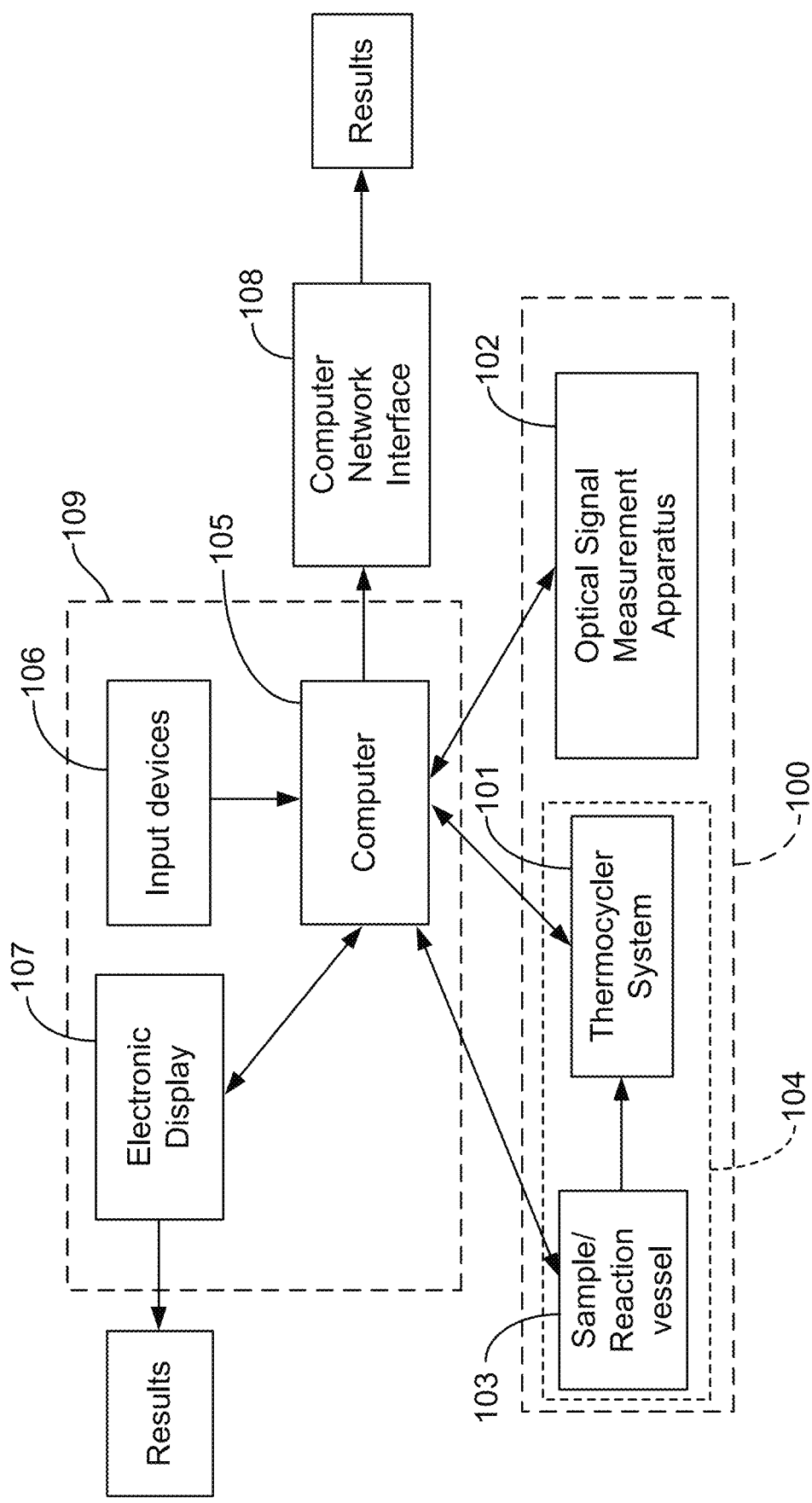
FIG. 1 is a schematic depicting an example system, in accordance with some embodiments.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of the claims.

A better understanding of the features and advantages of the present disclosure will be obtained by reference to the following detailed description that sets forth illustrative embodiments, in which the principles of embodiments of the present disclosure are utilized, and the accompanying drawings.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

The term "sample" us used herein may generally refer to a biological sample of a subject. The sample may be a tissue sample, such as a biopsy, core biopsy, needle aspirate, or fine needle aspirate. The sample may be a fluid sample, such as a blood sample, urine sample, or saliva sample. The sample may be a skin sample, a cheek swab. The sample may be a plasma or serum sample.

Nucleic acids may be isolated from one or more samples. As used herein, the term "nucleic acid" generally refers to a polymeric form of nucleotides of any length, either deoxyribonucleotides (dNTPs) or ribonucleotides (rNTPs), or analogs thereof. Non-limiting examples of nucleic acids include DNA, RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs.

The term "nucleic acid modification" may generally refer to modifications made to one or more nucleic acids. Modifications may include but are not limited to amplification, denaturation, elongation, primer extension reactions, nucleotide analog addition, etc.

As used herein, the term "reagents" generally refers to a composition comprising reaction mixtures necessary to complete nucleic acid modification (e.g., DNA amplification, RNA amplification), with non-limiting examples of such reagents that include primer sets having specificity for target RNA or target DNA, DNA produced from reverse transcription of RNA, a DNA polymerase, a reverse transcriptase (e.g., for reverse transcription of RNA), suitable buffers (including zwitterionic buffers), co-factors (e.g., divalent and monovalent cations), dNTPs, and other enzymes (e.g., uracil-DNA glycosylase (UNG)), etc.). Reagents may also comprise reporter agents or fluorescent dyes for incorporation in to an amplified product. In some cases, reagents can also comprise one or more reporter agents. Reagents may be lyophilized, stabilized or in a solution. Stabilization of the reagents may be performed using hydrogel or paraffin wax. Other methods of stabilizing, lyophilizing such reagents known to one of ordinary skill in the art may be used.

The term "polymerase," as used herein, generally refers to any enzyme capable of catalyzing a polymerization reaction. Polymerases may be used extend primers with the incorporation of nucleotides or nucleotide analogs. Examples of polymerases include, without limitation, a nucleic acid polymerase. The polymerase can be naturally occurring or synthesized. In some cases, a polymerase has relatively high processivity. An example polymerase is a Φ29 polymerase or a derivative thereof. Examples of polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof.

As used herein, the terms "amplifying" and "amplification" are used interchangeably and generally refer to generating one or more copies or "amplified product" of a nucleic acid. Non-limiting examples of nucleic acid amplification methods include reverse transcription, primer extension, polymerase chain reaction, ligase chain reaction, helicase-dependent amplification, asymmetric amplification, rolling circle amplification, and multiple displacement amplification (MDA). In cases where DNA is amplified, various DNA amplification methods may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). Amplification may be used to incorporate nucleotides and/or nucleotide analogs in to a growing chain of nucleic acids. PCR may be employed with thermal cycling or isothermally (i.e., isothermal PCR). Reporter agents such as fluorescent dyes may be used to identify target nucleic acids.

Reporter agents may be linked with nucleic acids, including amplified products, by covalent or non-covalent means. Non-limiting examples of non-covalent means include ionic interactions, Van der Waals forces, hydrophobic interactions, hydrogen bonding, and combinations thereof. In some embodiments, reporter agents may bind to initial reactants and changes in reporter agent levels may be used to detect amplified product. In some embodiments, reporter agents may only be detectable (or non-detectable) as nucleic acid amplification progresses. In some embodiments, an optically-active dye (e.g., a fluorescent dye) may be used as a reporter agent. Non-limiting examples of dyes include SYBR green, EvaGreen, LCGreen, SYBR blue, DAPI, propidium iodine, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-aminomethyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-aminonaphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores.

The present disclosure relates to methods and systems for nucleic acid modification and detection. The systems and methods may be used to detect multiple target nucleic acids samples and sequences. The methods and systems may be used as point of care testing devices for detection of infectious diseases, genetic abnormalities amongst other uses.

An example system for amplifying a target nucleic acid according to methods described herein is depicted in FIG. 1. The system comprises a computer 105, also referred to as a processor, that may serve as part of both the input and output modules. A user enters a sample/reaction vessel 103 comprising a reaction mixture ready for nucleic acid modification into the thermocycler system 101. In some cases, sample/reaction vessel 103 may be a sample preparation module that prepares the sample and loads the sample into a reaction vessel. The thermocycler system 101 may be attached to an optical signal measurement apparatus 102. The input and output module 109 comprises processor 105 and associated input devices 106 (e.g., tablets, keyboard, mouse, etc.) that can receive the user's request to amplify a target nucleic acid in the reaction mixture. The processor 105 may use electronic display 107 to send requests for modification of target sample preparation. The input and output module 109 communicates the user's request to the sample module 100 and nucleic acid modification commences in the thermocycler system 101. As modification proceeds, the optical signal measurement apparatus 102 of the sample module detects the amplified product. Information (e.g., raw data obtained by the detector) regarding the amplified product is transmitted from the optical signal measurement apparatus 102 back to the processor 105, which also serves as a component of the input and output module 109. The processor 105 receives the information from the sample module 104 performs any additional manipulations to the information, and then generates results containing the processed information. Results may be in the form of a report. Once the results are generated, the processor 105 then transmits the report to its end recipient over a computer network (e.g., an intranet, the internet) via computer network interface 108, in various forms.

Figure 2A:
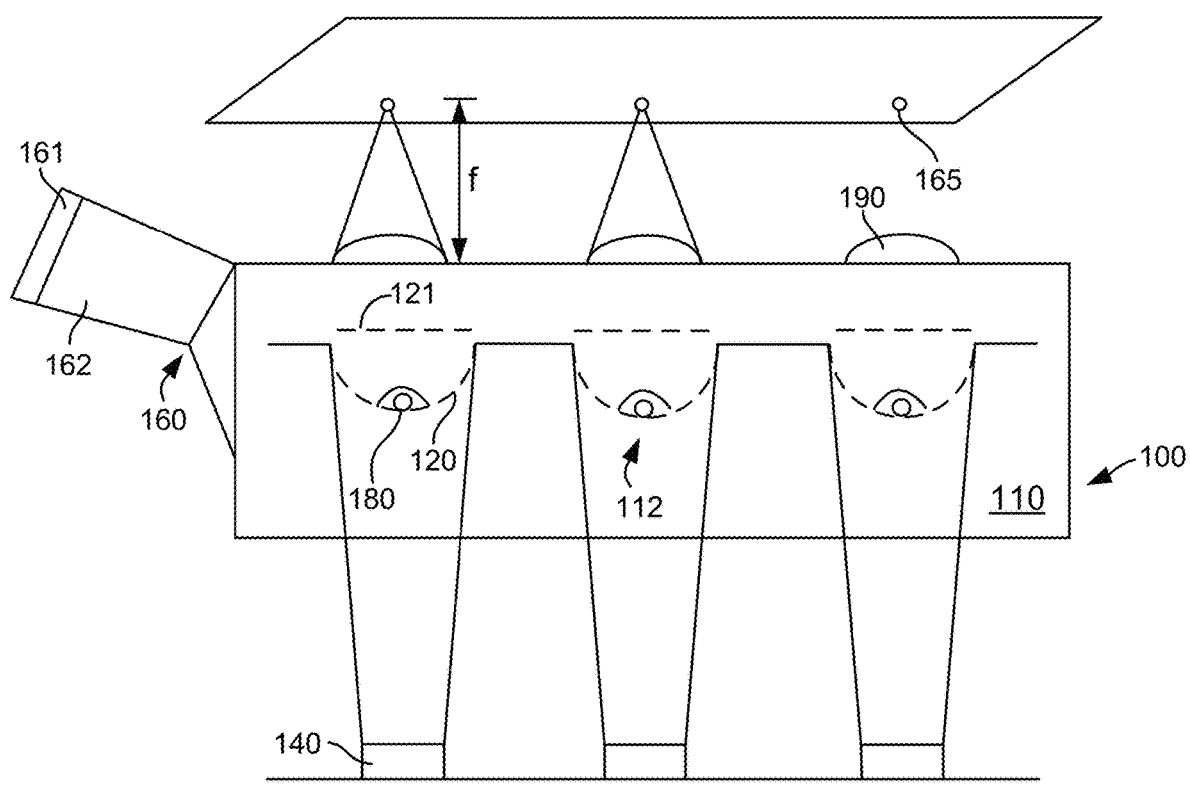
FIG. 2A is a schematic of the system, which may be used for modification of nucleic acids, in accordance with some embodiments.
Figure 2B:
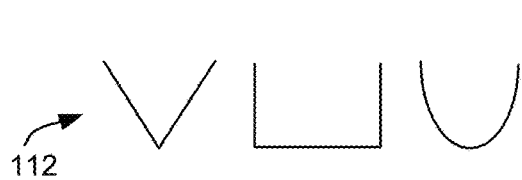
FIG. 2B is an illustration of shapes of wells or intrusions in a system, in accordance with some embodiments.

FIG. 2A illustrates an example of the sample module 100. In some embodiments, a system or a sample module may include a transparent block 110. Transparent block may be a conventional PCR block. Transparent block may comprise transparent polymers, polydimethysiloxane (PDMS), glass, polymethylmethacrylate (PMMA), cyclic olefin copolymer (COC) and or quartz. The transparent block 110 may have one or more intrusions or wells 112 to removably place a reaction vessel 130 illustrated in FIG. 4. Intrusions 112 in the transparent block may be conical, hemispherical, pyramidal, rectangular, cylindrical, truncated or dome-shaped. Some examples of the shapes of the intrusions in the transparent block have been shown in FIG. 2B. The intrusions may be the shape of a conventional PCR tube, strip or plate. The number of intrusions in a transparent block may be at least 8, 12, 14, 24, 36, 48, 96, 100 or 384 wells. The distance between each intrusion may be the same as the distance between the wells of a conventional PCR tube or plate.

Figure 4:
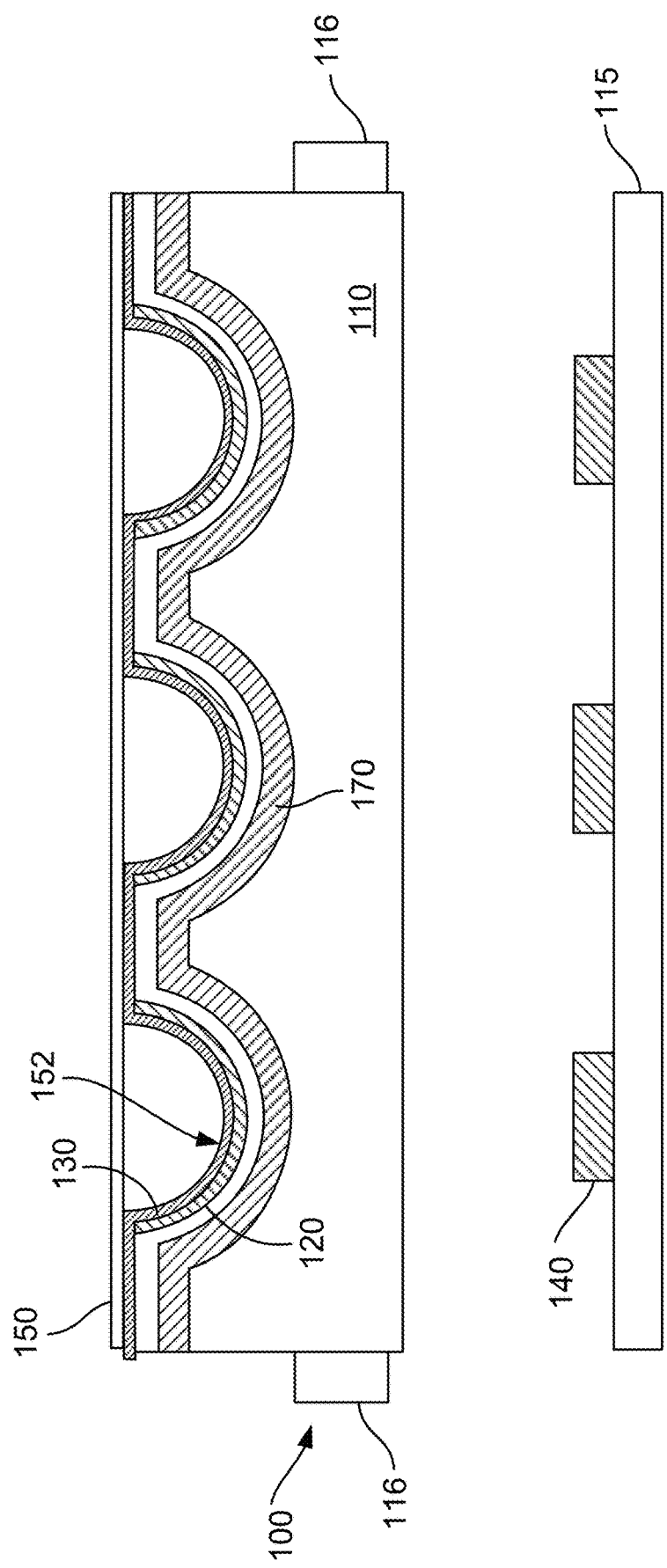
FIG. 4 is a schematic of a system with a fluid channel, in accordance with some embodiments.

Reaction vessels 130 as illustrated in FIG. 4 may include conventional PCR tubes, strips or plates. Reaction vessels may be conical, hemispherical, pyramidal, rectangular, cylindrical, truncated or dome-shaped. Some examples of the shapes of wells in reaction vessels have been shown in FIG. 2B. Reaction vessels may comprise thermoplastic polymers including polystyrene, polypropylene, poly (methyl methacrylate), cyclic olefin copolymer, polycarbonate and/or their derivatives. In some cases, the thickness of the reaction vessel may be 0.01 mm to 4 mm. In some cases, the thickness of the reaction vessel may be at least 0.01 mm. In some cases, the thickness of the reaction vessel may be at most 4 mm. In some cases, the thickness of the reaction vessel may be 4 mm to 3 mm, 4 mm to 2 mm, 4 mm to 1 mm, 4 mm to 0.5 mm, 4 mm to 0.1 mm, 4 mm to 0.05 mm, 4 mm to 0.01 mm, 3 mm to 2 mm, 3 mm to 1 mm, 3 mm to 0.5 mm, 3 mm to 0.1 mm, 3 mm to 0.05 mm, 3 mm to 0.01 mm, 2 mm to 1 mm, 2 mm to 0.5 mm, 2 mm to 0.1 mm, 2 mm to 0.05 mm, 2 mm to 0.01 mm, 1 mm to 0.5 mm, 1 mm to 0.1 mm, 1 mm to 0.05 mm, 1 mm to 0.01 mm, 0.5 mm to 0.1 mm, 0.5 mm to 0.05 mm, 0.5 mm to 0.01 mm, 0.1 mm to 0.05 mm, 0.1 mm to 0.01 mm, or 0.05 mm to 0.01 mm. In some cases, the thickness of the reaction vessel may be less than 4 mm, 3 mm, 2 mm, 1 mm, 0.5 mm, 0.1 mm, 0.05 mm, or 0.01 mm.

Figure 3:
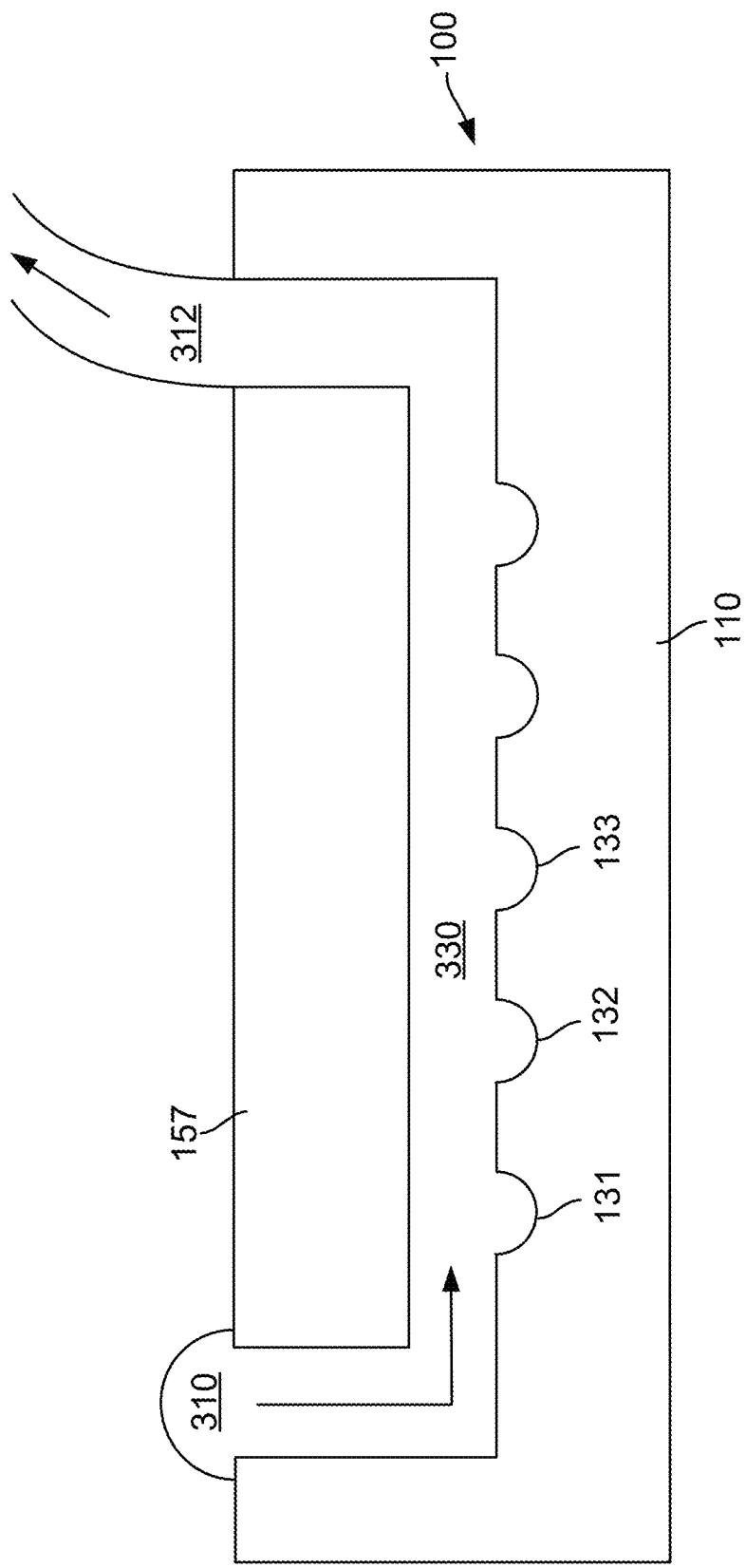
FIG. 3 is an illustration of the system with an inlet channel and an outlet, in accordance with some embodiments.

In some cases, the transparent block 110 may be used as a reaction vessel as is shown in FIG. 3. Transparent block 110 may comprise intrusions which may be used as reaction wells 131, 132, 133, etc. In such cases, the system may be part of a microfluidic system wherein sample input and output may be performed using ports. The transparent block 110 may comprise one or more inlet ports 310 for the loading of samples and reagents as shown in FIG. 3. In some cases, the transparent block may comprise one or more outlet ports 312.

As shown in FIG. 2A, the reaction vessel may comprise one or more light absorbing layers 120. In some cases, the transparent block with reaction wells (as shown in FIG. 3) may comprise a light absorbing layer 120. In some cases, the light absorbing material 120 may be in direct contact with reagents 180. In some embodiments, the light absorbing material may not be in direct contact with the reagents. In some cases, the light absorbing material may have a passivation layer (not shown here) to prevent inhibition of enzymes. In some cases, one or more wells in a reaction vessel may comprise 2-D or 3-D microstructures or nanostructures in the form of one or more pillar arrays, 1D or 2D grating structures, photonic crystals or hemispheres.

The light absorbing layer 120 may be in the shape of the reaction vessel. In some cases, the reaction vessel may be covered by the light absorbing layer. In some cases, a light absorbing layer may be deposited on the surface of the well. In some cases, the thickness of the light absorbing layer may be 1 nm to 1 mm. In some cases, the thickness of the light absorbing layer may be at least 1 nm. In some cases, the thickness of the light absorbing layer may be at most 1 mm. In some cases, the thickness of the light absorbing layer may be 1 nm to 50 nm, 1 nm to 100 nm, 1 nm to 500 nm, 1 nm to 1,000 nm, 1 nm to 0.01 mm, 1 nm to 0.05 mm, 1 nm to 0.1 mm, 1 nm to 0.5 mm, 1 nm to 1 mm, 50 nm to 100 nm, 50 nm to 500 nm, 50 nm to 1,000 nm, 50 nm to 0.01 mm, 50 nm to 0.05 mm, 50 nm to 0.1 mm, 50 nm to 0.5 mm, 50 nm to 1 mm, 100 nm to 500 nm, 100 nm to 1,000 nm, 100 nm to 0.01 mm, 100 nm to 0.05 nm, 100 nm to 0.1 mm, 100 nm to 0.5 mm, 100 nm to 1 mm, 500 nm to 1,000 nm, 500 nm to 0.01 mm, 500 nm to 0.05 mm, 500 nm to 0.1 mm, 500 nm to 0.5 mm, 500 nm to 1 mm, 1,000 nm to 0.01 mm, 1,000 nm to 0.05 mm, 1,000 nm to 0.1 mm, 1,000 nm to 0.5 mm, 1,000 nm to 1 mm, 0.01 mm to 0.05 mm, 0.01 mm to 0.1 mm, 0.01 mm to 0.5 mm, 0.01 mm to 1 mm, 0.05 mm to 0.1 mm, 0.05 mm to 0.5 mm, 0.05 mm to 1 mm, 0.1 mm to 0.5 mm, 0.1 mm to 1 mm, or 0.5 mm to 1 mm. In some cases, the thickness of the light absorbing layer may be 1 nm, 50 nm, 100 nm, 500 nm, 1,000 nm, 0.01 mm, 0.05 mm, 0.1 mm, 0.5 mm, or 1 mm. Reaction vessels may comprise a lower light absorbing layer 120 and an upper absorbing layer 121. The upper light absorbing layer may be a part of the sealing film.

Light absorbing layer 120 may comprise a layer of metals. Non-limiting examples of metals that may be used are gold (Au), silver (Ag), nickel (Ni), titanium (Ti), chromium (Cr), germanium (Ge), palladium (Pd), ruthenium (Ru), tungsten (W), iridium (Ir), or platinum (Pt). In some cases, the light absorbing layer is an alloy. Light absorbing material may be a carbon base, non-limiting examples of which include carbon nanotubes, graphite, graphene and/or graphene oxide. Light absorbing layer may comprise of paints such as acrylic paints. Light absorbing layer may comprise a mixture of a metal, metal alloy, carbon base or paint. In some cases, more than one layer of light absorbing materials may be used. One light absorbing layer may absorb light from a light source and transmit light which is not absorbed at first light absorbing layer to the second light absorbing layer to generate heat. Light absorbing materials used may be thin to maintain high heating and cooling rates.

Figure 2C:
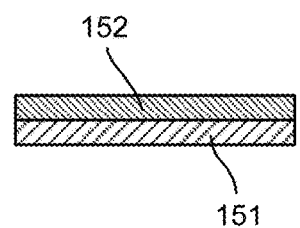
FIG. 2C and 2D are schematics of sealing films to be used with a system, in accordance with some embodiments.
Figure 2D:
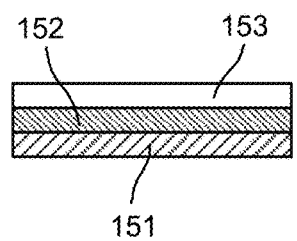

A reaction vessel may be sealed with a sealing film 150 as discussed more fully with respect to FIG. 4. The sealing film may comprise adhesives. In some cases, the sealing film may comprise a light absorbing layer 152. The light absorbing layer in the sealing film may help in maintaining a uniform temperature in the reaction vessel. A sealing film may comprise aluminum, polyolefin, polypropylene, polyester, polycarbonate, polystyrene and other commercially used sealing film materials. A sealing film may be a conventional PCR plate sealing film. In some cases, a sealing film may be colored to absorb light. A sealing film may comprise multiple layers as shown in FIGS. 2C-2D. The sealing film may have a layer of adhesive material 151. In addition to the adhesive material 151, the sealing film may have a layer of light absorbing material and/or a colored film 152 as shown in FIG. 2C. In some cases, in addition to the adhesive material, the sealing film may comprise a layer of light absorbing material 152 and a layer of transparent, conventionally used PCR film 153 as shown in FIG. 2D. The thickness of a sealing film may range from about 50 µm to about 255 µm.

As shown in FIG. 2A, the system may have one or more light sources 140. The light sources in a system may be the primary source of heat for the reaction vessel. The system may comprise one light source per system. Alternatively, the system may comprise more than one light source. In some cases, the number of light sources in a system is the same as the number of intrusions in the transparent block. Each intrusion of the transparent block may be in contact with one or more light sources. In some cases, each intrusion of a transparent block may be in thermal communication with a single light source. In some cases, different wells/intrusions may be able to maintain different thermal profiles based on their light source. For instance, a well in a reaction vessel may be maintained at 65° C. and another well may be maintained at 60° C. based on their light sources. The emitting area or chip size of the light sources may cover the size of the intrusions in the transparent block. Light sources may be light-emitting diode (LED), laser diode (LD), tungsten lamp, fluorescent lamp, halogen lamp, mercury lamp, xenon lamp, metal halide lamp or combinations thereof.

In some embodiments, the wavelength of the light sources may be in a range that does not coincide with the wavelength of fluorescent dyes. Non-limiting examples of wavelengths of light source include: 400 nm, 405 nm, 440 nm, 445 nm, 460 nm, 650 nm, 720 nm, 850 nm and 950 nm.

In some cases, the heating rate of a light absorbing material may be dependent on the light source. Using a 3 W LED as an example of a light source, the heating rate of a light absorbing material by a light source may be between 2° C./sec and 20° C./sec. In some cases, the heating rate may be about 2° C./sec to about 20° C./sec. In some cases, the heating rate may be at least about 5° C./sec. In some cases, the heating rate may be at most about 20° C./sec. In some cases, the heating rate may be about 2° C./sec to about 3° C./sec, about 5° C./sec to about 7° C./sec, about 5° C./sec to about 10° C./sec, about 5° C./sec to about 13° C./sec, about 5° C./sec to about 15° C./sec, about 5° C./sec to about 18° C./sec, about 5° C./sec to about 20° C./sec, about 7° C./sec to about 10° C./sec, about 7° C./sec to about 13° C./sec, about 7° C./sec to about 15° C./sec, about 7° C./sec to about 18° C./sec, about 7° C./sec to about 20° C./sec, about 10° C./sec to about 13° C./sec, about 10° C./sec to about 15° C./sec, about 10° C./sec to about 18° C./sec, about 10° C./sec to about 20 ° C./sec, about 13° C./sec to about 15° C./sec, about 13° C./sec to about 18° C./sec, about 13° C./sec to about 20° C./sec, about 15° C./sec to about 18° C./sec, about 15° C./sec to about 20° C./sec, or about 18° C./sec to about 20° C./sec. In some cases, the heating rate may be about 5° C./sec, about 7° C./sec, about 10° C./sec, about 13° C./sec, about 15° C./sec, about 18° C./sec, or about 20° C./sec. Heating rates may be different in higher or lower power light sources.

In some cases, the light-to-heat conversion efficiency may be dependent on the wavelength and light output power of a light source, the thickness of a light absorbing material and the distance between the light source and the light absorbing material. In some cases, the light-to-heat efficiency is at least 40%, at least 45%, at least 50%, at least 55%, at least 60%, at least 65%, at least 70%, at least 75%, at least 80%, at least 85%, at least 90% or at least 95%.

A system may comprise an optical signal measurement apparatus (OSM) 160. OSM apparatus may comprise one or more excitation sources 161. In some cases, an apparatus may comprise one excitation source. In some cases, an apparatus may comprise more than one excitation source. The excitation source may be placed above the transparent block or on the sides of the transparent block. In some cases, excitation sources may be LEDs. The LEDs are excitation sources that may be used to generate light at desired wavelengths to excite labels used for detecting nucleic acid products during real-time PCR, dissociation behavior during thermal melt analysis, and/or nucleic acid related assays. The excitation sources may be used to excite the one or more fluorescent dyes in the reaction vessel. Examples of fluorescent dyes that may be used may be any fluorescent dye described herein and as known to one of ordinary skill in the art. Non-limiting examples of wavelengths of the excitation sources include 460 nm, 440 nm, 470 nm, 500 nm, 600 nm, 650 nm, 700 nm.

The optical measurement apparatus may further comprise one or more optical filters 162. The optical filters may be used to allow only selected wavelengths to reach a fluorescent dye in the reaction vessels and wells in the apparatus. Optical filters could be used, at the output of the LEDs/lasers or both to suppress any unwanted light (e.g. light emitted by the LED aside from the center wavelength peak). The OSM may comprise multiple filters such as a filter that may allow the excitation source wavelength, a filter that allows the emission source wavelength, a filter to reduce or eliminate the light from the light source used for heating amongst others. Filters may include but are not limited to long pass filters for wavelengths between 400-560 nm, for example, 530 long pass filter, or short pass filters for wavelengths between 800-900 nm, for example a 840 nm short pass filter.

The OSM may further comprise one or more sensors or detectors 165 to detect the signal from the reaction vessel. The sensor may be a CMOS sensor, CCD sensor, photodiode or a spectrophotometer. The apparatus may comprise one or more photodiode per well of the reaction vessel. The sensor may be used to detect the modification of one or more nucleic acid targets.

Figure 2E:
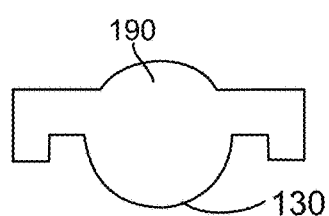
FIG. 2E is a schematic of the placement of an embedded lens above a reaction vessel, in accordance with some embodiments.

The system may further comprise one or more embedded lenses 190 to focus the light from the reaction vessel and direct it towards the sensor 165. FIG. 2E illustrates an example of an embedded lens 190 above a reaction vessel 130. Embedded lens 190 may be integrated with other elements of the optical system as described herein. There may be one sensor per reaction vessel. In some cases, there may be more than one lens per reaction vessel. Alternatively, there may be a lens for each well of the reaction vessel. The embedded lens may be placed between the light source and the transparent block. Alternatively, the embedded lens may be placed between a detector region in the OSM and the reaction vessel.

The system may also comprise one or more temperature sensors (not shown). The one or more temperature sensors may be placed inside the reaction vessel, on the surface of the reaction vessel, embedded in the wall of the reaction vessel or on the surface of the light absorbing layer. The system may comprise one temperature sensor per reaction vessel or the number of temperature sensors may be equal to the number of wells in the reaction vessel. Temperature sensors may include thermocouples, IR temperature sensors, resistance temperature detectors, thermistor sensors and other sensors as are known to one of ordinary skill in the art.

As shown in FIG. 2A, reagents 180 may be added to one or more wells of a reaction vessel. Reagents may be lyophilized. Lyophilized reagents may be coated with a hydrogel or paraffin wax. Samples and reagents may be added to the wells in the reaction vessel using valves or ports (shown in FIG. 3). The reagents may be placed on to the wells individually or through a channel. The system may comprise of one or more channel networks. The one or more channel networks may be microfluidic channel networks. Sample or reagents may be added to individual wells or through such a channel 330 as shown in FIG. 3. A cover plate or lid 157 can be utilized in conjunction with the microfluidic channel networks illustrated in FIG. 3.

The system in FIG. 3 and systems described in other embodiments may comprise one or more valves. The wells of the reaction vessel may be pre-loaded with different reagent before the thermal cycling is initiated. The one or more valves may prevent mixing of reagent solution between the wells on the reaction vessel. Non-limiting examples of valves that may be used include solenoid valves, screw valves, pneumatic valves, etc. In some cases, each well in the reaction vessel may have access to one or more valves. Valves may be placed between each reaction well, between the inlet and first wells and/or between the outlet and the last wells in the reaction vessel.

Another embodiment of the system is illustrated in FIG. 4. The transparent block 110 may be placed above a base 115. The transparent block may be coupled to side supports 116 and can be placed using the side supports. The side supports may assist in maintaining a certain distance between the light source and the transparent block. System 100 may comprise a transparent block 110 with a fluid circulation channel 170. A cross section of the transparent block with the channel 170 is shown in FIG. 4. The fluid channel may be used to circulate any fluids during thermal cycling. Fluids may include, water, air, coolant liquids and other fluids. The fluid flowing through the fluid circulation channel may be transparent so as not to interfere with the light emission from the light source 140. The fluid circulation channel may be designed to have a shape similar to the shape of the intrusions in the reaction vessel and the transparent block. During thermal cycling, different fluids may be cycled in the circulation channel. For example, in a cooling phase, water or a coolant liquid may be circulated to cool down the reaction vessel. In some cases, air may be circulated during thermal cycling. Fluids may be circulated using conventional pumps known in the field.

Fluids may be circulated through the fluid circulation channel for at least 1 second to at most 60 seconds. In some cases, fluid is circulated in the channel for about 1 second to about 60 seconds. In some cases, fluid is circulated in the channel for at least about 1 second. In some cases, fluid is circulated in the channel for at most about 60 seconds. In some cases, fluid is circulated in the channel for about 1 second to about 5 seconds, about 1 second to about 10 seconds, about 1 second to about 20 seconds, about 1 second to about 30 seconds, about 1 second to about 40 seconds, about 1 second to about 50 seconds, about 1 second to about 60 seconds, about 5 seconds to about 10 seconds, about 5 seconds to about 20 seconds, about 5 seconds to about 30 seconds, about 5 seconds to about 40 seconds, about 5 seconds to about 50 seconds, about 5 seconds to about 60 seconds, about 10 seconds to about 20 seconds, about 10 seconds to about 30 seconds, about 10 seconds to about 40 seconds, about 10 seconds to about 50 seconds, about 10 seconds to about 60 seconds, about 20 seconds to about 30 seconds, about 20 seconds to about 40 seconds, about 20 seconds to about 50 seconds, about 20 seconds to about 60 seconds, about 30 seconds to about 40 seconds, about 30 seconds to about 50 seconds, about 30 seconds to about 60 seconds, about 40 seconds to about 50 seconds, about 40 seconds to about 60 seconds, or about 50 seconds to about 60 seconds. In some cases, fluid is circulated in the channel for about 1 second, about 5 seconds, about 10 seconds, about 20 seconds, about 30 seconds, about 40 seconds, about 50 seconds, or about 60 seconds.

In this example, the light absorbing material 120 is placed on the intrusions of the transparent block 110 instead of inside the reaction vessel 130. In such cases, any conventional PCR plate may be used as a reaction vessel combined with a conventional sealing film or a sealing film described herein. In other examples, the light absorbing layer 120 may be placed in the reaction vessel. As discussed in relation to FIG. 2C, a layer of light absorbing material 152 may be incorporated as an element of a sealing film, illustrated in FIG. 4 as sealing film 150.

Figure 5:
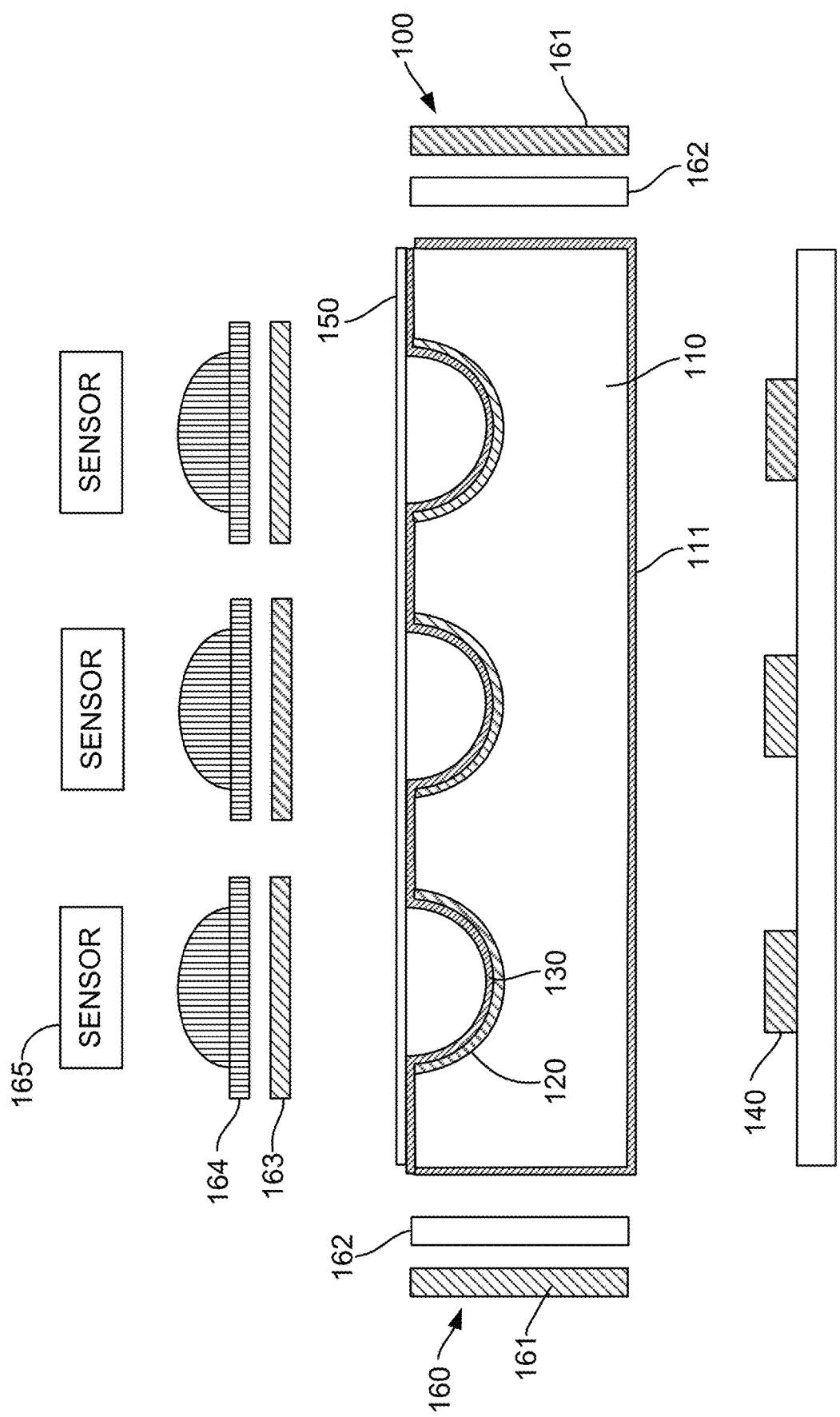
FIG. 5 is a schematic of a system with a detailed view of the optical signal measurement apparatus, in accordance with some embodiments.

Another embodiment of the system is shown in FIG. 5. Transparent block 110 with a light absorbing layer placed in the intrusions may have a reaction vessel sealed with a sealing film 150. In addition, the transparent block may be covered on the outside with a high refractive index film 111. When light from the light source or the excitation source enters the transparent block covered with a film with high refractive index, the angle of refraction may be smaller than the angle of incidence and the light may be refracted towards the normal of the surface for a more uniform transmission of light in to the wells of the reaction vessel.

Also illustrated in FIG. 5 is an embodiment of the OSM apparatus 160. The OSM apparatus may comprise one or more excitation sources 161. The one or more excitation sources may be configured to excite one or more fluorescent dyes used in the nucleic acid modification assays. Fluorescent dyes and their corresponding excitation sources may be any commonly used ones as are known to one of ordinary skill in the art. More than one type of excitation sources may be used in one OSM apparatus. For instance, the OSM apparatus may comprise an excitation source with the wavelength 460 nm to excite dyes such as FAM, SYBR green, etc. in addition to an excitation source with a wavelength of 440 nm to excite dyes such as LC Green.

The OSM apparatus may also comprise one or more optical filters. In this example, an optical filter 162 may be placed in front of the excitation source. This optical source may be configured to only allow the excitation light wavelength. For example, for an excitation source of wavelength 460 nm, an optical filter 162 may be a 480 nm short pass filter. Other optical filters known in the art may also be used. In addition to the optical filter 162, the OSM apparatus may also comprise a first filter 164 and a second filter 163. The second filter 163 placed above the reaction vessel may be used as an elimination filter to remove the light from light source 140. For instance, the second filter 163 may be a filter specific for elimination of 800-850 nm wavelength. The second filter may be a Distributed Bragg reflector (DBR) with high reflectivity over the emission wavelength of the light source. The first filter may be used as an emission filter. The emission filter may only allow light emitted from the reaction vessel as a result of the excitation of a fluorescent dye in the reaction vessel. For instance, the first filter or the emission filter may be a long pass filter specific to allow light with wavelength of 470-530 nm. Any conventional filters, known to a person of ordinary skill in the art may be used. The OSM apparatus may also comprise sensors 165 as described previously herein.

Figure 6:
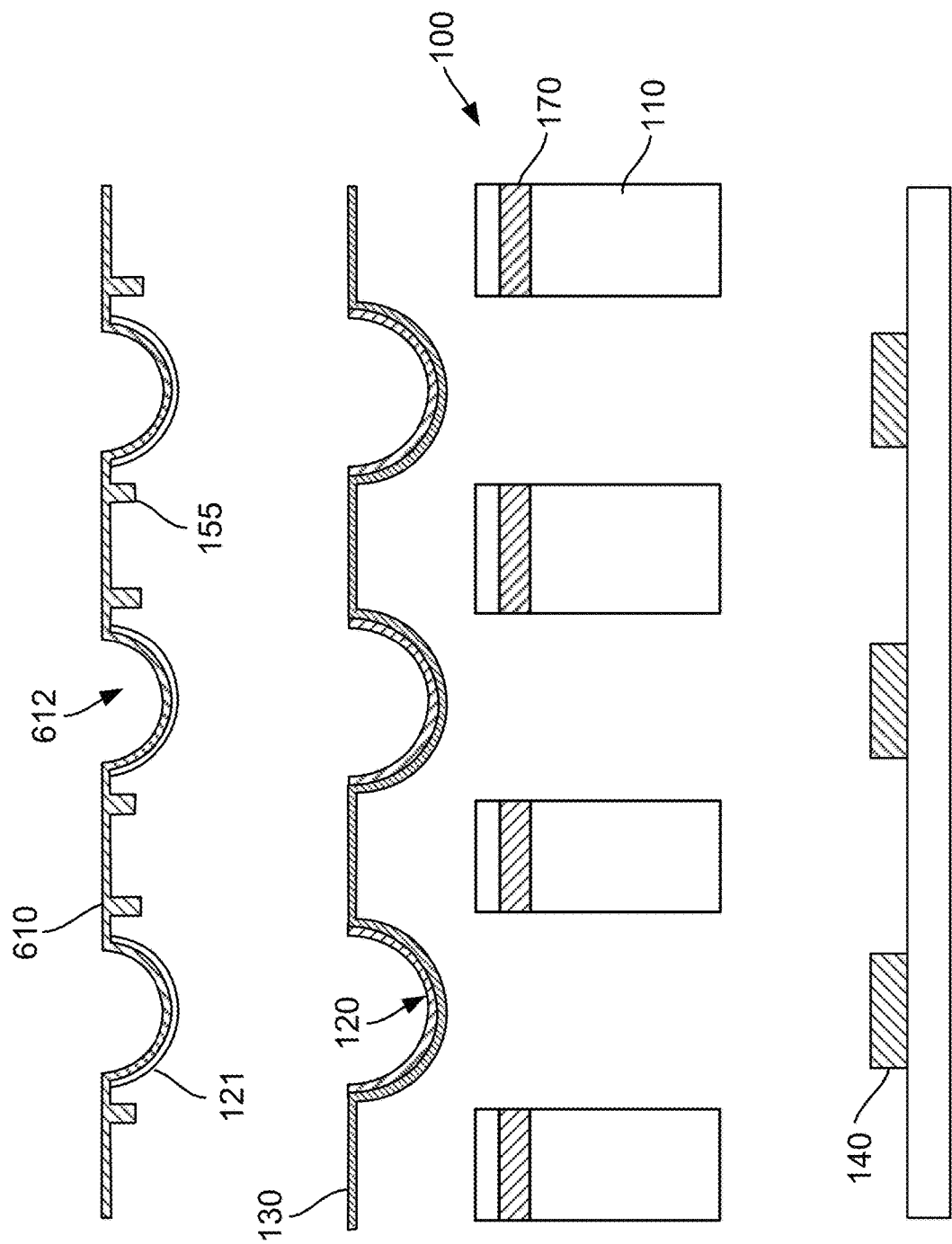
FIG. 6 is an exploded view of a schematic of a system, in accordance with some embodiments.
Figure 7:
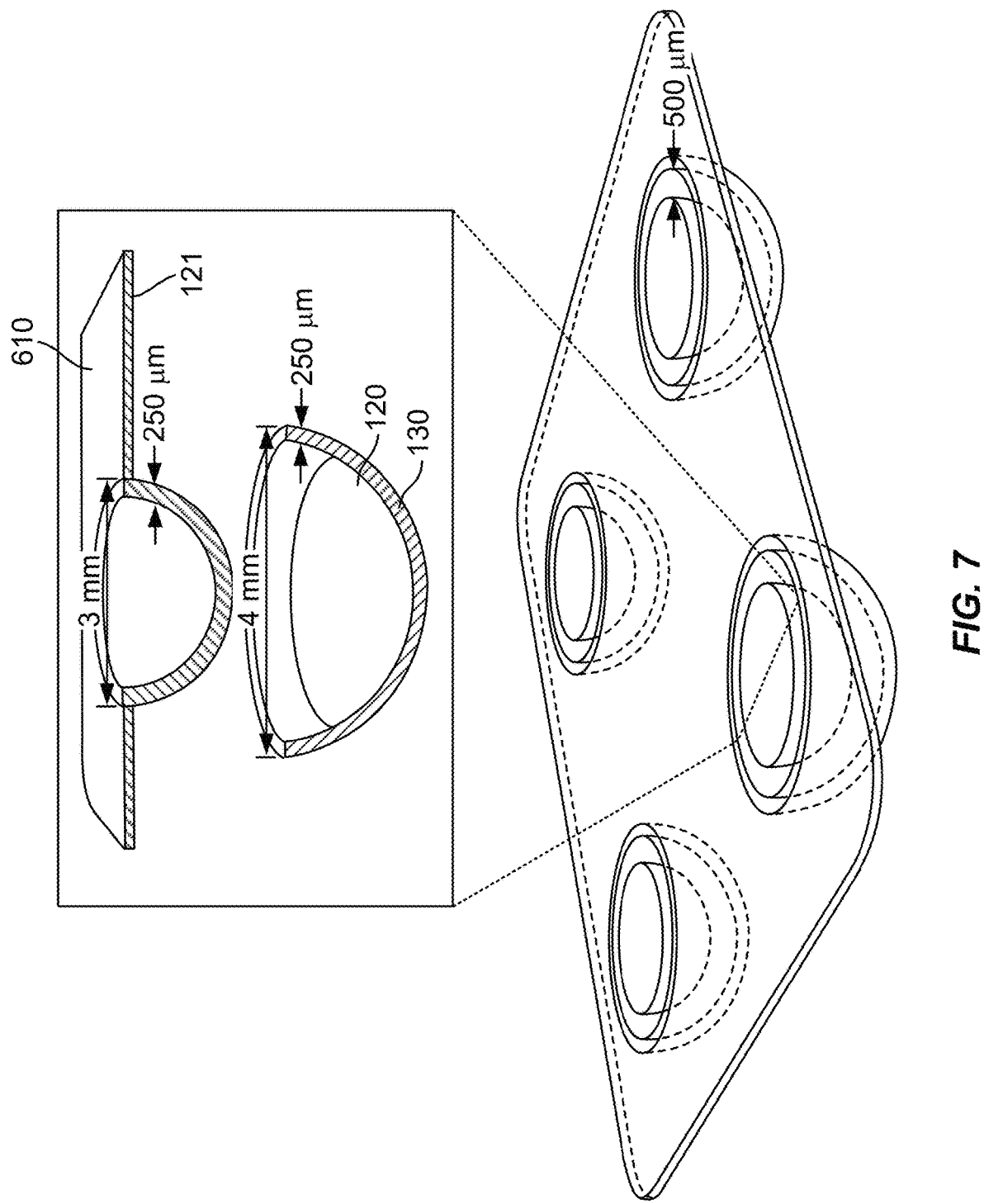
FIG. 7 is a schematic and dimensions of a reaction vessel system, in accordance with some embodiments.
Figure 8:
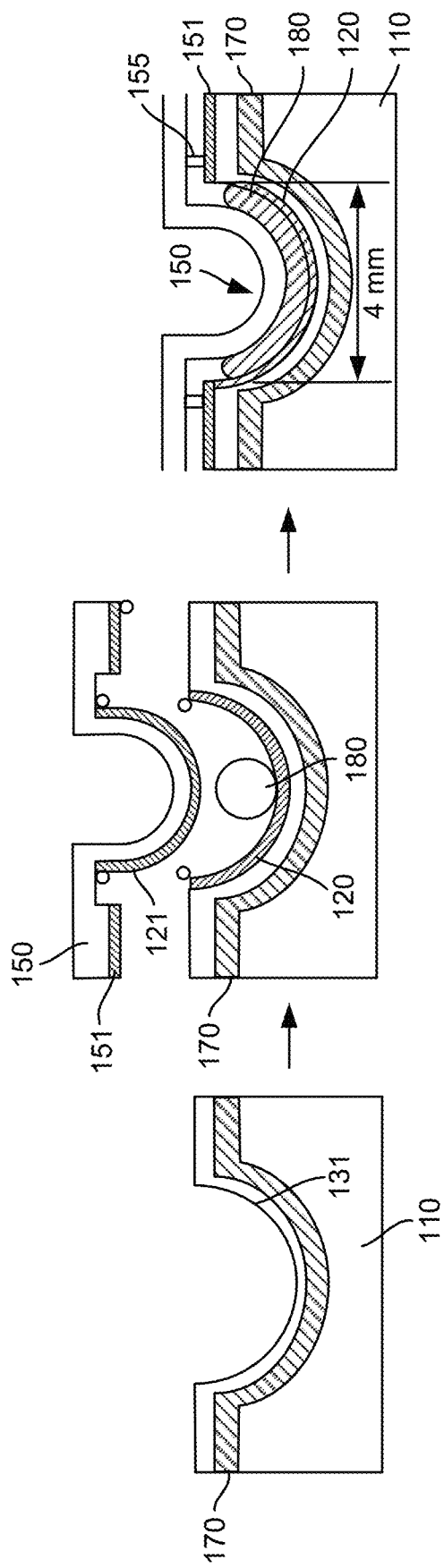
FIG. 8 is a schematic depiction of the mechanism of loading a system, in accordance with some embodiments.

Another embodiment of the system is illustrated in FIGS. 6-8. FIG. 6 is an exploded view of the system in a cross-section view. The transparent block 110 may comprise intrusions (not shown here) and a fluid circulation channel 170 as previously described. Components of the system may be coupled to supports that are not shown in the cross-section illustrated in FIG. 6. A reaction vessel 130, as described previously may be removably placed on the transparent block 110. In some embodiments, the light absorbing material 120 may be removably placed on the reaction vessel 130. The sample may be placed in the reaction vessel in direct contact with the light absorbing layer. A sealing plate 610 may be removably placed on the reaction vessel 130.

The sealing plate 610 may be made of the same material as the reaction vessel. The sealing plate may have intrusions 612 shaped similar to the wells of the reaction vessel as shown in FIG. 6. Portions or all of the bottom surface of the sealing plate may be covered with a light absorbing material 121. The sealing plate may also comprise spacers 155.

FIG. 7 shows the mechanism of using a sealing plate 610 with the system. A transparent block with reaction wells 130 with the wells covered with a light absorbing layer 120 may be placed on the transparent block. Reagents and samples may be placed in the wells of the reaction well 130. A sealing plate 610 with intrusions, the shape of the wells of the reaction vessel, may be placed on top of the reaction vessels. The bottom layer of the sealing plate 610 may comprise a layer of light absorbing material 121. The corners of the sealing plate may comprise an adhesive layer 151 as illustrated in FIG. 8 to seal the reaction vessel and the sealing plate. The sealing plate may also comprise spacers 155 as illustrated in FIG. 8. The spacers can be used to maintain a space between the sealing plate and the reaction vessel.

Upon sealing, sample and reagents 180 may get uniformly distributed in the reaction vessel covered on both sides with light absorbing layers 120 and 121. A reaction vessel may comprise a lower light absorbing layer and an upper light absorbing layer wherein the reaction vessel may be defined to be between the two light absorbing layers. The reaction vessel and the sealing plate may be used as supports for the light absorbing layers with a first light absorbing material disposed on a first support to define a reaction well and a second light absorbing material disposed on a second support opposite the first support as part of the sealing plate.

The volume of the sample and reagents used in such a system may be configured to leave air gaps between the sample and the corners of the sealing plate. The system may have a fluid circulation channel (not shown here) for uniform cooling of the reaction vessel.

FIG. 8 illustrates the embodiments of FIG. 7 in greater depth. The bottom plate may comprise reaction wells (such as 131) covered with a layer of light absorbing material 120. The thickness of the light absorbing layer 120 may be from 1 nm to 1 mm. In this example, the thickness of the reaction well (131) is 250 µm. The wells in the reaction well may have a diameter ranging from 1 mm to 10 mm. In this example, the diameter of the reaction well shown is 4 mm. The reaction well may be used to contain a sample volume from 1 µl to 20 µl.

Sealing plate 610 may comprise one or more intrusions 612 as illustrated in FIG. 6. The diameter of the intrusion in the sealing plate may be smaller than the diameter of the wells in the reaction well to leave space for the sample and reagents. The diameter of the intrusions in the sealing plate may be from 0.5 mm to 8 mm. In this example, the diameter of the sealing plate is 3 mm. Sealing plate 150 comprising a layer of light absorbing material 121 may be placed on top of the reaction well. The thickness of the light absorbing layer may be the same as layer 120. In some embodiments, the thickness of the light absorbing layer may be less or more than the thickness of layer 120. In some cases, layers 120 and 121 may be made of the same material. For instance, in one example both layer 120 and 121 are made of a metal such as gold or chromium. In some alternative embodiments, layers 120 and 121 may be made of different materials. For instance, layer 120 may be made of a metal such as gold and layer 121 may be made of a carbon based material.

Modifications of nucleic acids may comprise identifying a target nucleic acid from a sample. A PCR reaction using the systems discussed herein may be performed for such modifications. A sample containing nucleic acids may be added to reagents (lyophilized, stabilized or in a solution) in the presence of a buffer solution. The mixture may then undergo thermal cycling through a range of temperatures to complete the amplification process. Thermal cycling may include multiple cycles such as a denaturation cycle, an annealing cycle, an elongation cycle and/or an incubation cycle.

In some embodiments, the reagents 180 may be placed in the wells of the reaction well 130 of the systems discussed herein. The reagents may be in the form of lyophilized beads or pellets. Stabilization of the reagents may be performed using a hydrogel or paraffin wax. The hydrogel or paraffin may have a melting temperature higher than room temperature. Reagents and samples may be loaded on to the wells of the reaction well using channel, pumps and valves as described herein or as are known to one of ordinary skill in the art.

Upon loading and sealing, the system may generate an amplified product through thermal cycling. Thermal cycling may comprise one or more cycles of incubating a reaction mixture at a denaturation temperature for a denaturation time period followed by incubating the mixture at an annealing temperature for an annealing time period further followed by incubating the mixture at an elongation temperature for an elongation time period. A system may heat the wells of the reaction well 130 (not shown) by using one or more light sources 140 (not shown) as previously described. Focused light by lens between the one or more light sources and the reaction well may be used also. The embedded lens may be used to focus emission from the fluorescent dye integrated in the reaction vessel/wells. For the cooling of the sample and reagents, the one or more light sources may be turned off for a cooling time period. In some cases, a fluid circulation channel 170 may be used as previously described for the cooling of the reagents and samples in the wells of the reaction well.

Amplification a sample may be performed by using the systems described previously to perform one or more thermal cycles comprising a denaturation cycle, an annealing cycle and an elongation cycle. The time in which an amplification reaction may yield a detectable result in the form of an amplified product may vary depending on the target nucleic acid, the sample, the reagents used and the protocol for PCR. In some cases, an amplification process may be performed in less than 1 minute. In some cases, an amplification process may be performed in about 1 minute to about 40 minutes. In some cases, an amplification process may be performed in at least about 1 minute. In some cases, an amplification process may be performed in at most about 40 minutes. In some cases, an amplification process may be performed in about 1 minute to about 5 minutes, about 1 minute to about 10 minutes, about 1 minute to about 15 minutes, about 1 minute to about 20 minutes, about 1 minute to about 25 minutes, about 1 minute to about 30 minutes, about 1 minute to about 35 minutes, about 1 minute to about 40 minutes, about 5 minutes to about 10 minutes, about 5 minutes to about 15 minutes, about 5 minutes to about 20 minutes, about 5 minutes to about 25 minutes, about 5 minutes to about 30 minutes, about 5 minutes to about 35 minutes, about 5 minutes to about 40 minutes, about 10 minutes to about 15 minutes, about 10 minutes to about 20 minutes, about 10 minutes to about 25 minutes, about 10 minutes to about 30 minutes, about 10 minutes to about 35 minutes, about 10 minutes to about 40 minutes, about 15 minutes to about 20 minutes, about 15 minutes to about 25 minutes, about 15 minutes to about 30 minutes, about 15 minutes to about 35 minutes, about 15 minutes to about 40 minutes, about 20 minutes to about 25 minutes, about 20 minutes to about 30 minutes, about 20 minutes to about 35 minutes, about 20 minutes to about 40 minutes, about 25 minutes to about 30 minutes, about 25 minutes to about 35 minutes, about 25 minutes to about 40 minutes, about 30 minutes to about 35 minutes, about 30 minutes to about 40 minutes, or about 35 minutes to about 40 minutes. In some cases, an amplification process may be performed in about 1 minute, about 5 minutes, about 10 minutes, about 15 minutes, about 20 minutes, about 25 minutes, about 30 minutes, about 35 minutes, or about 40 minutes.

In some cases, amplification of a sample may be performed by repeating the thermal cycle 5 to 40 times. In some cases, the thermal cycle may be repeated at least 5 times. In some cases, the thermal cycle may be repeated at most 60 times. In some cases, the thermal cycle may be repeated 5 times, 10 times, 15 times, 20 times, 25 times, 30 times, 35 times 40 times, 45 times, 50 times, 55 times or 60 times.

A thermal cycle may be completed in a thermal cycling time period. In some cases, a thermal cycling time period may range from 2 seconds to 60 seconds per cycle. In some cases, a thermal cycle may be completed in about 2 seconds to about 60 seconds. In some cases, a thermal cycle may be completed in at least about 2 seconds. In some cases, a thermal cycle may be completed in at most about 60 seconds. In some cases, a thermal cycle may be completed in about 2 seconds to about 5 seconds, about 2 seconds to about 10 seconds, about 2 seconds to about 20 seconds, about 2 seconds to about 40 seconds, about 2 seconds to about 60 seconds, about 5 seconds to about 10 seconds, about 5 seconds to about 20 seconds, about 5 seconds to about 40 seconds, about 5 seconds to about 60 seconds, about 10 seconds to about 20 seconds, about 10 seconds to about 40 seconds, about 10 seconds to about 60 seconds, about 20 seconds to about 40 seconds, about 20 seconds to about 60 seconds, or about 40 seconds to about 60 seconds. In some cases, a thermal cycle may be completed in about 2 seconds, about 5 seconds, about 10 seconds, about 20 seconds, about 40 seconds, or about 60 seconds.

The temperature and time period of the denaturation cycle may be dependent on the properties sample to be identified, the reagents and the amplification protocol being used. A denaturation cycle may be performed at temperatures ranging from about 80° C. to about 110° C. A denaturation cycle may be performed at a temperature of at least about 80° C. A denaturation cycle may be performed at a temperature of at most about 110° C. A denaturation cycle may be performed at a temperature of about 80° C. to about 85° C., about 80° C. to about 90° C., about 80° C. to about 95° C., about 80° C. to about 100° C., about 80° C. to about 105° C., about 80° C. to about 110° C., about 85° C. to about 90° C., about 85° C. to about 95° C., about 85° C. to about 100° C., about 85° C. to about 105° C., about 85° C. to about 110° C., about 90° C. to about 95° C., about 90° C. to about 100° C., about 90° C. to about 105° C., about 90° C. to about 110° C., about 95° C. to about 100° C., about 95° C. to about 105° C., about 95° C. to about 110° C., about 100° C. to about 105° C., about 100° C. to about 110° C., or about 105° C. to about 110° C. A denaturation cycle may be performed at a temperature of about 80° C., about 85° C., about 90° C., about 95° C., about 100° C., about 105° C., or about 110° C.

In some cases, the time period of a denaturation cycle may be less than about 1 second. In some cases, the time period of a denaturation cycle may be at most about 100 seconds. In some cases, the time period of a denaturation cycle may be about 0 second to 1 second, about 1 second to about 5 seconds, about 1 second to about 10 seconds, about 1 second to about 20 seconds, about 1 second to about 40 seconds, about 1 second to about 60 seconds, about 1 second to about 100 seconds, about 5 seconds to about 10 seconds, about 5 seconds to about 20 seconds, about 5 seconds to about 40 seconds, about 5 seconds to about 60 seconds, about 5 seconds to about 100 seconds, about 10 seconds to about 20 seconds, about 10 seconds to about 40 seconds, about 10 seconds to about 60 seconds, about 10 seconds to about 100 seconds, about 20 seconds to about 40 seconds, about 20 seconds to about 60 seconds, about 20 seconds to about 100 seconds, about 40 seconds to about 60 seconds, about 40 seconds to about 100 seconds, or about 60 seconds to about 100 seconds. In some cases, the time period of a denaturation cycle may be less than about 1 second, about 5 seconds, about 10 seconds, about 20 seconds, about 40 seconds, about 60 seconds, or about 100 seconds.

The temperature and time period of the annealing and elongation cycles may be dependent on the properties sample to be identified, the reagents and the amplification protocol being used. An annealing and/or elongation cycle may be performed at a temperature of about 40° C. to about 70° C. An annealing and/or elongation cycle may be performed at a temperature of at least about 40° C. An annealing and/or elongation cycle may be performed at a temperature of at most about 70° C. An annealing and/or elongation cycle may be performed at a temperature of about 40° C. to about 45° C., about 40° C. to about 50° C., about 40° C. to about 55° C., about 40° C. to about 60° C., about 40° C. to about 65° C., about 40° C. to about 70° C., about 45° C. to about 50° C., about 45° C. to about 55° C., about 45° C. to about 60° C., about 45° C. to about 65° C., about 45° C. to about 70° C., about 50° C. to about 55° C., about 50° C. to about 60° C., about 50° C. to about 65° C., about 50° C. to about 70° C., about 55° C. to about 60° C., about 55° C. to about 65° C., about 55° C. to about 70° C., about 60° C. to about 65° C., about 60° C. to about 70° C., or about 65° C. to about 70° C. An annealing and/or elongation cycle may be performed at a temperature of about 40° C., about 45° C., about 50° C., about 55° C., about 60° C., about 65° C., or about 70° C.

In some cases, the time period of an annealing and/or elongation cycle may be less than about 1 second. In some cases, the time period of an annealing and/or elongation cycle may be at most about 60 seconds. In some cases, the time period of an annealing and/or elongation cycle may be about 0 seconds to 1 seconds, about 1 second to about 5 seconds, about 1 second to about 10 seconds, about 1 second to about 20 seconds, about 1 second to about 40 seconds, about 1 second to about 60 seconds, about 5 seconds to about 10 seconds, about 5 seconds to about 20 seconds, about 5 seconds to about 40 seconds, about 5 seconds to about 60 seconds, about 10 seconds to about 20 seconds, about 10 seconds to about 40 seconds, about 10 seconds to about 60 seconds, about 20 seconds to about 40 seconds, about 20 seconds to about 60 seconds, or about 40 seconds to about 60 seconds. In some cases, the time period of an annealing and/or elongation cycle may be less than about 1 second, about 5 seconds, about 10 seconds, about 20 seconds, about 40 seconds, or about 60 seconds.

In some cases, a cooling cycle may be performed between the denaturation cycle and annealing and/or elongation cycles. In some cases, a cooling cycle may be performed for about 1 second to about 60 seconds. In some cases, a cooling cycle may be performed for at least about 1 second. In some cases, a cooling cycle may be performed for at most about 60 seconds. In some cases, a cooling cycle may be performed for about 1 second to about 5 seconds, about 1 second to about 10 seconds, about 1 second to about 20 seconds, about 1 second to about 30 seconds, about 1 second to about 40 seconds, about 1 second to about 50 seconds, about 1 second to about 60 seconds, about 5 seconds to about 10 seconds, about 5 seconds to about 20 seconds, about 5 seconds to about 30 seconds, about 5 seconds to about 40 seconds, about 5 seconds to about 50 seconds, about 5 seconds to about 60 seconds, about 10 seconds to about 20 seconds, about 10 seconds to about 30 seconds, about 10 seconds to about 40 seconds, about 10 seconds to about 50 seconds, about 10 seconds to about 60 seconds, about 20 seconds to about 30 seconds, about 20 seconds to about 40 seconds, about 20 seconds to about 50 seconds, about 20 seconds to about 60 seconds, about 30 seconds to about 40 seconds, about 30 seconds to about 50 seconds, about 30 seconds to about 60 seconds, about 40 seconds to about 50 seconds, about 40 seconds to about 60 seconds, or about 50 seconds to about 60 seconds. In some cases, a cooling cycle may be performed for about 1 second, about 5 seconds, about 10 seconds, about 20 seconds, about 30 seconds, about 40 seconds, about 50 seconds, or about 60 seconds.

Detection of the amplified product using OSM 160 as described previously may be performed at various stages of the amplification process. In some cases, the detection of an amplified product may be performed at the end of the amplification process. In some cases, the detection of the amplified product may be performed during a thermal cycle. Alternatively, in some cases, detection may be performed at the end of each thermal cycle. In addition to the detection methods described herein, detection of an amplified product may be performed using gel electrophoresis, capillary electrophoresis, sequencing, short tandem repeat analysis and other methods as are known to one of ordinary skill in the art.

Light absorbing material placed in the system for modification of nucleic acids, as described in any of the embodiments herein, may be in the form of a solid shape as shown in FIG. 9A. FIG. 9A shows the light absorbing material as a circle but it may be in different shapes, such as the shape of the reaction wells or the intrusions in the transparent block. In some cases, the light absorbing material may have one or more open areas. In some cases, the light absorbing material may have one open area 910 in the center, such as shown in FIG. 9B. The open area 910 in the center of the light absorbing material, which can represent either light absorbing material 120 or light absorbing material 121 as illustrated in FIG. 2A, or both, may be used to direct light from an excitation source for the detection of fluorescence in the reaction mixture. In some cases, the light absorbing material may have more than one open areas as shown in FIG. 9C. Multiple open areas 912 may be used to direct different excitation sources to the fluorescent material in the reaction mixture or the same excitation source light may be directed using multiple open areas in the light absorbing material. The open areas in a light absorbing material may only be on the light absorbing materials in the reaction vessel. In some cases, light absorbing material in the sealing film or sealing plate may also have one or more open areas. In some cases, light absorbing material in both a reaction well and in a sealing film/plate may have open areas.

In some cases, the percentage of open area in a light absorbing material may be about 1% to about 90%. In some cases, the percentage of open area in a light absorbing material may be at least about 1%. In some cases, the percentage of open area in a light absorbing material may be at most about 90%. In some cases, the percentage of open area in a light absorbing material may be about 1% to about 10%, about 1% to about 20%, about 1% to about 50%, about 1% to about 70%, about 1% to about 90%, about 10% to about 20%, about 10% to about 50%, about 10% to about 70%, about 10% to about 90%, about 20% to about 50%, about 20% to about 70%, about 20% to about 90%, about 50% to about 70%, about 50% to about 90%, or about 70% to about 90%. In some cases, the percentage of open area in a light absorbing material may be about 1%, about 10%, about 20%, about 50%, about 70%, or about 90%.

Figure 10:
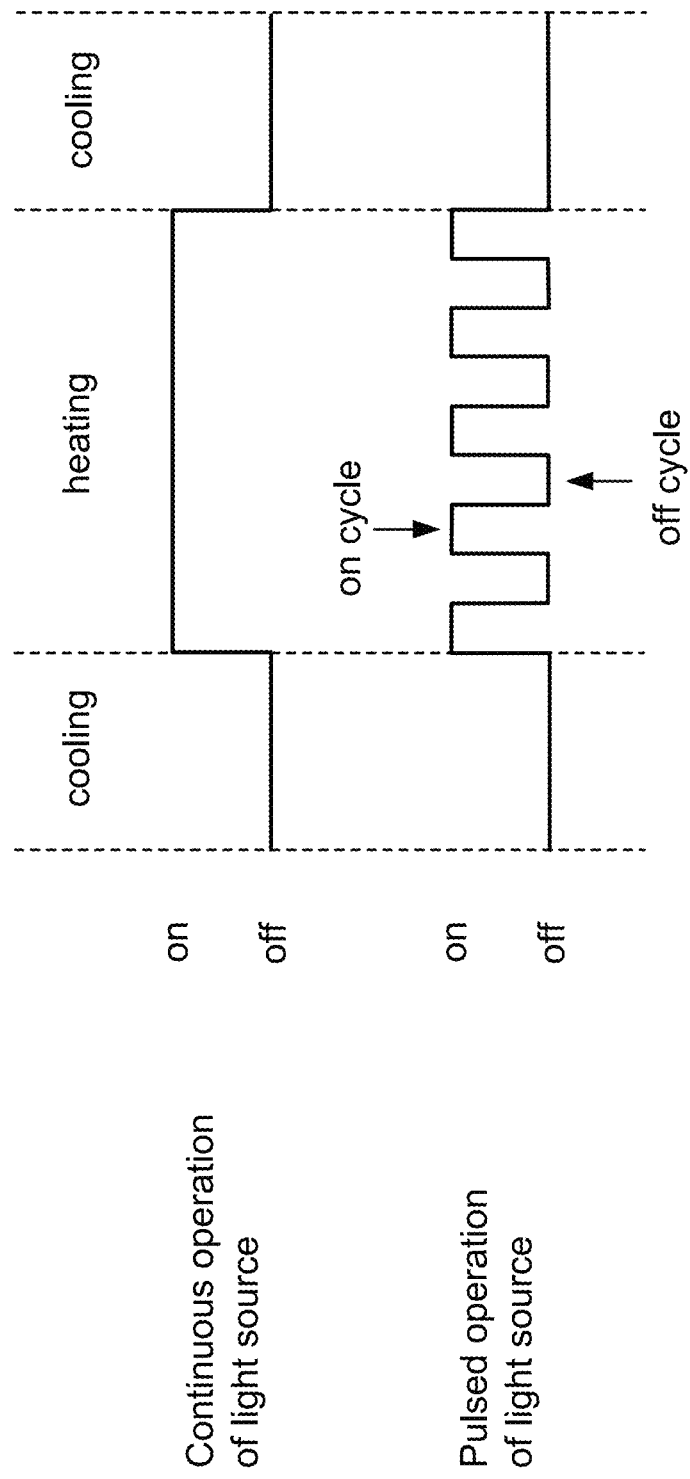
FIG. 10 is a schematic depiction of continuous and pulsed operation of the light source, in accordance with some embodiments.

Operation of the light source may be performed in a continuous or a pulsed manner. In some cases, the operation of the light source is continuous, for instance as shown in FIG. 10. In some cases, for every heating cycle including denaturation, annealing and extension cycles, the light source can be operated to increase temperature for denaturation. This may be performed by applying a certain injection current to the light source. To maintain the temperature for annealing/extension, the injection current of the light source may be adjusted without turning off the light source. The light source may be turned off during the cooling cycle.

In some cases, the light source may be operated in a pulsed manner, as shown in FIG. 10. For every heating cycle, the light source may be turned on and off repeatedly at short intervals. In some cases, the intervals for each cycle can be modified for instance, the denaturation cycle may have shorter intervals of pulses as compared to a lower annealing temperature. In some cases, the injection current to the light source may be modified during a pulsing cycle. The light source may be turned off during the cooling cycle.

In some embodiments, operation of the excitation source may be pulsed. In some cases, the pulsed operation of the excitation source may be performed in an alternating manner as compared to the pulsing of the light source as shown in FIG. 11A. As the light source is pulsed to an off cycle, the excitation source may be turned on. As the light source is pulsed to an on cycle, the excitation source may be turned off. In some embodiments, detection of a signal may be performed parallel to the pulsing of the excitation source. The sensors detecting a fluorescent signal from the reaction wells may collect data in a pulsing manner parallel to the excitation source as shown in FIG. 11A. This may be performed to reduce or avoid optical interference between the light source and the excitation source or the interference between the light source and the fluorescence in the reaction wells which may be the result of a nucleic acid modification.

Figure 11B:
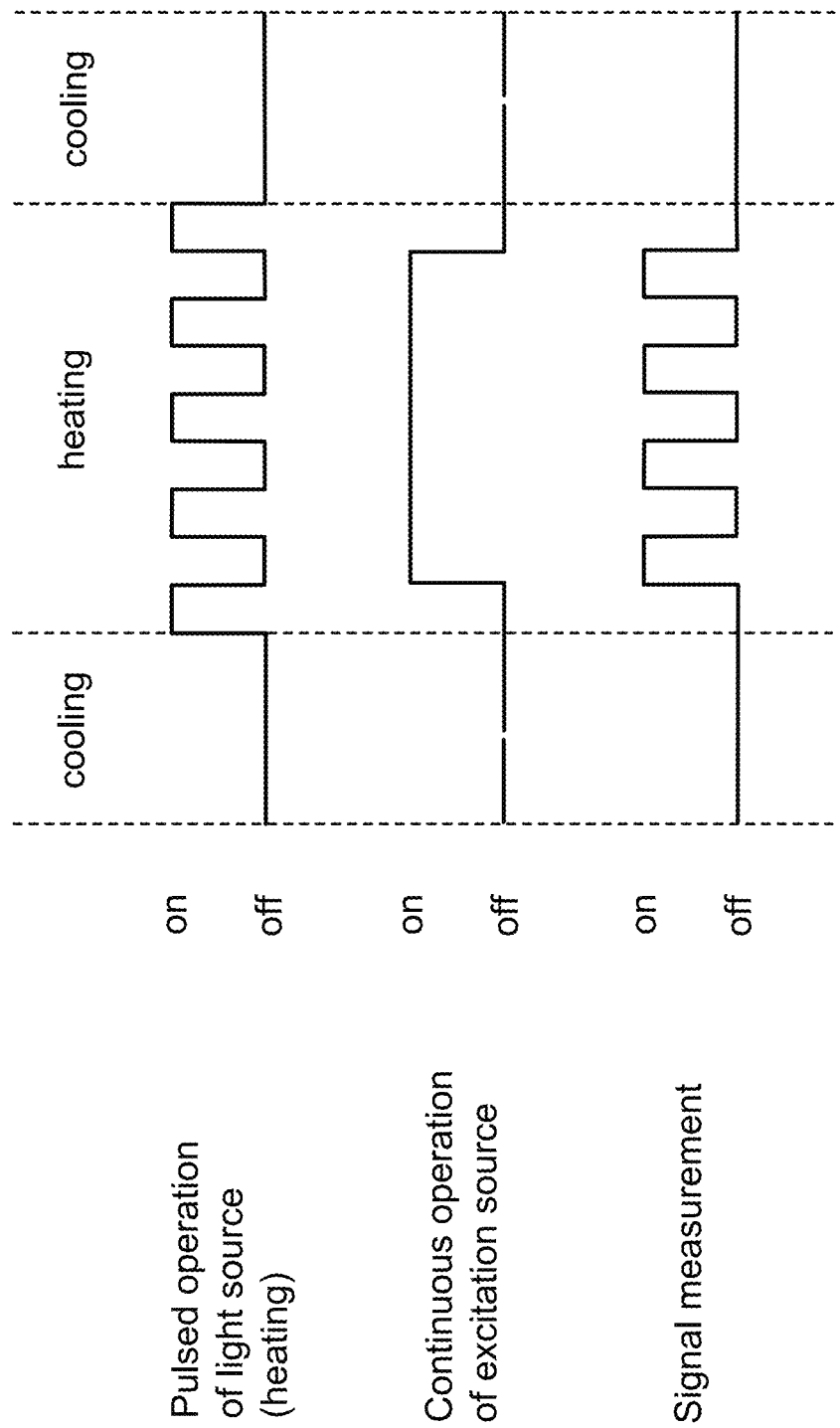
FIG. 11B is a schematic depiction of pulsed operation of the light source and continuous operation of the excitation source in conjunction with signal measurement, in accordance with some embodiments.

In other embodiments, operation of the excitation source may be continuous as illustrated in FIG. 11B and discussed in relation to FIG. 10. Thus, in some cases, the pulsed operation of the light source may be performed in an alternating manner while the operation of the excitation source is continuous. In some embodiments, detection of a signal may be performed parallel to the pulsing of the excitation source. The sensors detecting a fluorescent signal from the reaction wells may collect data in a pulsing manner parallel to the light source as shown in FIG. 11B. This may be performed to reduce or avoid optical interference between the light source and the excitation source or the interference between the light source and the fluorescence in the reaction wells which may be the result of a nucleic acid modification.

Sample Preparation

The systems for nucleic acid modification may in some cases include a system or module for sample preparation. The sample preparation system may be used for the concentration of a cell of interest. The cells of interest may be any specific target cell. For instance, the cell of interest may be red blood cells, platelets, leukocytes, infectious cells such as pathogens amongst other cell types. The sample preparation cell type may also be used to extract and purify nucleic acids from target cells. The sample used for the concentration of the target cell type may be any sample type described herein.

In some cases, the sample preparation system may be able to concentrate a cell type of interest from a biological sample, extract and purify nucleic acids from a sample in less than 15 minutes. In some cases, the sample preparation system may be able to extract and purify nucleic acids from a biological sample in less than 15 minutes, less than 12 minutes, less than 10 minutes, less than 8 minutes, less than 5 minutes, less than 2 minutes or less than 1 minute.

Figure 12:
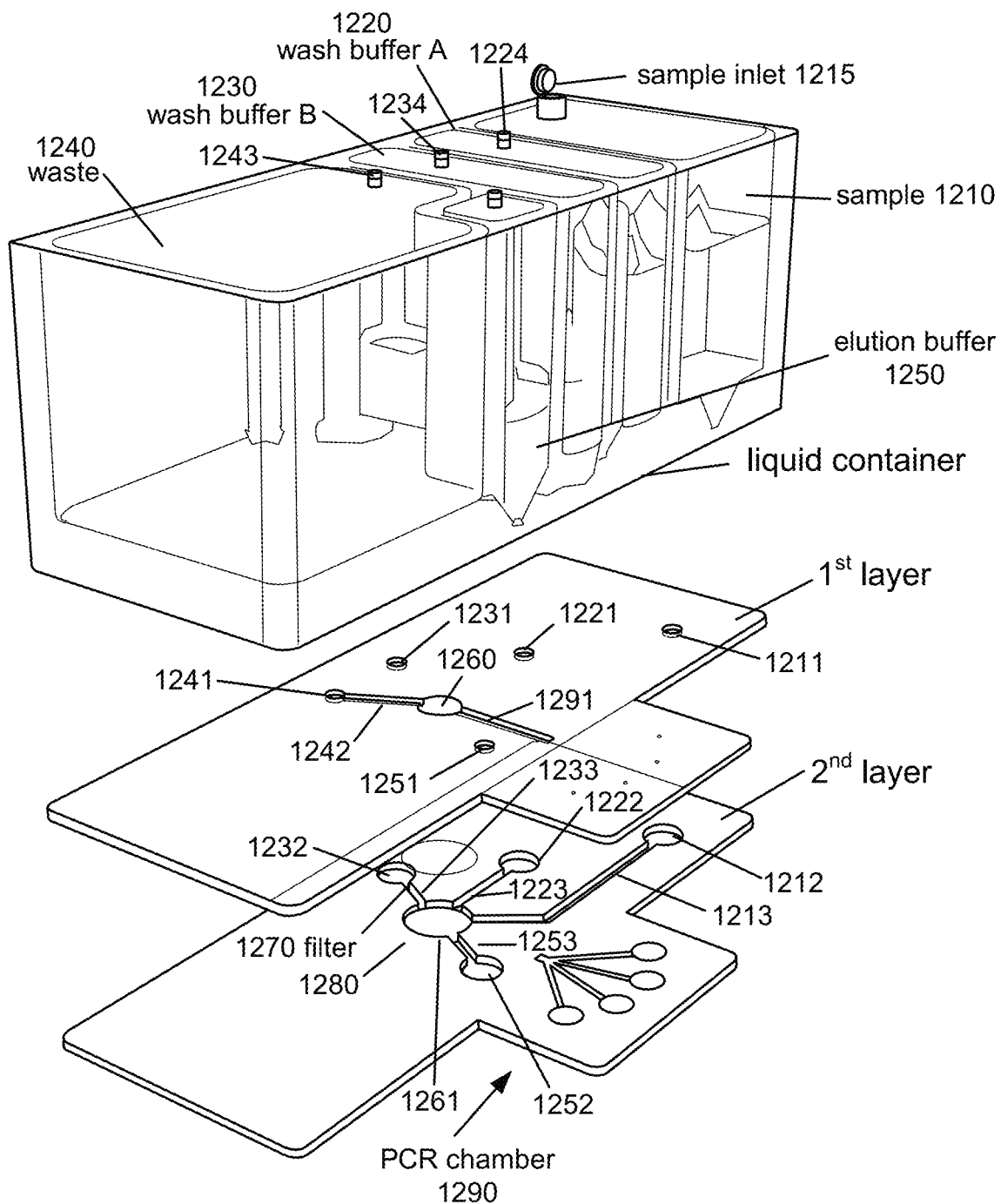
FIG. 12 is an exploded view of the sample preparation module with PCR reaction wells, in accordance with some embodiments.

Referring to FIG. 12, a system for sample preparation is shown. Sample preparation system 1200 may have multiple fluid compartments, such as a sample compartment 1210 to collect a biological sample, one or more wash buffer compartments 1220 and 1230, a waste compartment 1240 and an elution buffer compartment 1250. The one or more compartments of the sample preparation system may be connected to a collection area 1261 with a cover 1260 through various microfluidic channels, reservoirs and through-holes. The microfluidic system may be in the form of a replaceable cartridge in the sample preparation system.

A sample compartment may comprise a sample inlet 1215. The sample inlet 1215 may comprise a pre-filter for filtering out cells and debris and crystals by size. The pre-filter may be above the through-hole 1211 instead of at the sample inlet 1215. In some cases the pre-filter may have a pore size of 3 µm, 4 µm, 5 µm, 6 µm, 7 µm, 8 µm, 9 µm or 10 µm. The pre-filter may be able to remove non-target materials such as sediments and larger cells from a biological sample such as a urine sample.

Each compartment may have an air inlet. Each air inlet of a liquid container may be serially connected to a micro-solenoid valve and then to a pump. As shown in FIG. 12, each fluid compartment may have their specific air-inlets. For the sample compartment, sample inlet 1215 may also act as the air inlet. In some cases, the sample compartment may have a separate air-inlet. Also shown in FIG. 12 are air-inlets for wash buffer compartments 1224 and 1234, air-inlet 1243 for the waste compartment and air-inlet 1234 for the elution buffer compartment. The liquid outlets may be directly connected to the designated microchannels connected to each compartment. Microfluidic channels may be made of PDMS PMMA, COC, other conventional polymers and/or SU-8 silicon wafer.

The microfluidic channels may all be in a single layer or they may be divided over multiple layers of channels and collection areas, reservoirs or through-holes. For instance, in FIG. 12, shown are two layers of microfluidic channels, a first layer and a second layer. Multiple compartments in the sample preparation system may span over multiple layers of the microfluidic system. As shown in FIG. 12, a sample compartment may be connected to a through-hole 1211 in the first layer and through-hole 1211 may be connected to the reservoir 1212 in the second layer with a microfluidic channel 1213 which may be used to connect the sample compartment to the collection area 1261 with a cover 1260. Through-holes and reservoirs in the microfluidic system may be of the same shape and size. Alternatively, the reservoirs may in some cases, be larger than the through-holes. Through-holes and their corresponding reservoirs may be aligned together.

Similarly other compartments may also be connected. In FIG. 12, wash compartments 1220 and 1230 may be connected to through-holes 1221 or 1231 respectively, in the first layer. Through-holes 1221 and 1231 may be connected to reservoirs 1222 or 1232 in the second layer and connect to the collection area 1261 through channels 1223 and 1233 respectively. The waste compartment may also be connected to the microfluidic system using through-holes and channels.

As shown in FIG. 12, waste compartment 1240 may be connected to through-hole 1241 and also connects to the collection area 1261 through a channel 1242. Also shown in FIG. 12 is the elution buffer compartment 1250 connected to the microfluidic system by through-hole 1251 in the first layer, reservoir 1252 in the second layer and channel 1253 to connect the elution buffer compartment to the collection area 1261. FIG. 12 represents a system with one collection area and one channel leading from each compartment to the collection area but the sample preparation system may comprise multiple collection areas connected to multiple channels for each compartment.

Collection area 1261 may be in the shape of a well as shown in FIG. 12 and covered with a cover 1260. Collection area 1261 may comprise a filter 1270 between the cover 1260 and collection area 1261 for the entrapment and processing of one or more target cells. The sample preparation system may comprise more than one filter. A target cell type may be entrapped and treated for nucleic acid extraction and purification on one or more filters.

Collection area 1261 may also be covered with a light absorbing material 1280 for the photothermal lysis of target cells. In some cases, the collection area 1261 is covered with a light absorbing material 1280 and a filter 1270. The filter 1270 may be placed on top of the light absorbing material 1280. Alternatively, the light absorbing material 1280 may be below the collection area 1261. In such cases, the filter 1270 may be on the collection area. Photothermal lysis of a target cell may be performed by using a light source for the conversion of light to heat. Light sources may be any light sources described elsewhere herein and may be placed below the microfluidic system. In some cases, a filter 1270 entrapping one or more target cells may be placed above or near a light source and a light absorbing material 1280. Light absorbing material may be any light absorbing material described elsewhere herein. In FIG. 12, the microfluidic network is shown to be connected directly to a PCR compartment 1290 by channel 1291. In other examples, the microfluidic network may not be in the same cartridge as shown in FIG. 12. In such example, different air-inlets and pumps may be used for the movement of the sample nucleic acids to reaction wells as described elsewhere herein.

The sample preparation system may have one or more air inlets. The sample preparation system may have one or more pneumatic control valves. The pneumatic control valves may be a part of a pneumatic control system for sample fluid actuation. Pressurized air and control valves may be used for the movement of fluids from one reservoir to the other. A schematic of a sample processing using valves and air-inlets is shown in FIG. 13.

Figure 13A:
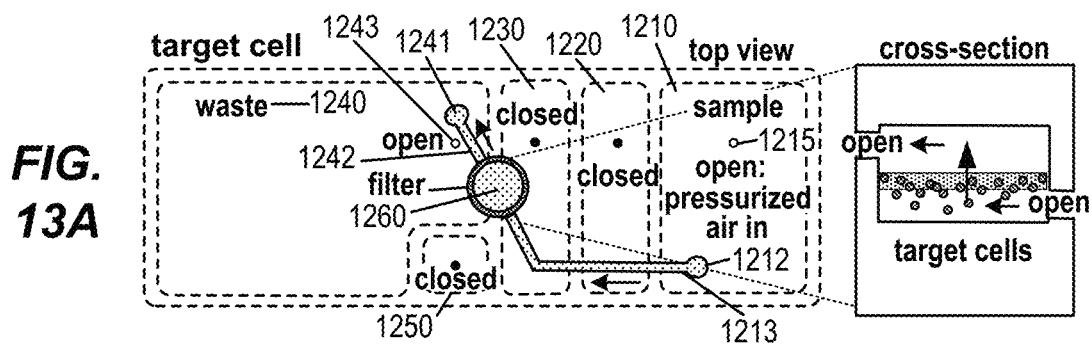
FIGS. 13A-13E are a schematic depiction of the sample preparation module in use, in accordance with some embodiments.

Referring to FIGS. 12 and 13A, after adding sample solution to the sample compartment, solenoid valves connected to the air-inlet and reservoir of the sample (1211, 1212) and waste (1241) compartments may be opened and pressurized air may be allowed in through air-inlet 1215 and through-hole 1211 of the sample compartment so that the pressure is only applied to the sample compartment. All of the other air-inlets may be closed so that the sample solution only passes through microfluidic channels 1213 and 1242. These channels may consist of two microfluidic layers, top and bottom layers. The channel 1213 connected to the sample compartment may be located in the second microfluidic layer (2nd layer shown in FIG. 12) and the channel 1242 on the waste side is located in the top layer (1st layer shown in FIG. 12). Overlapping between these channels may be the collection area 1261 comprising a filter 1270 to selectively isolate target cells. Filter 1270 may have a pore size that is specific for the target cells. Afterwards, the sample and waste compartments and their corresponding air-inlets may be closed by the solenoid valves for the next step. The sample compartment may have one or more electrodes placed around the compartment to change the pH of the solution by applying different voltages.

Figure 13B:
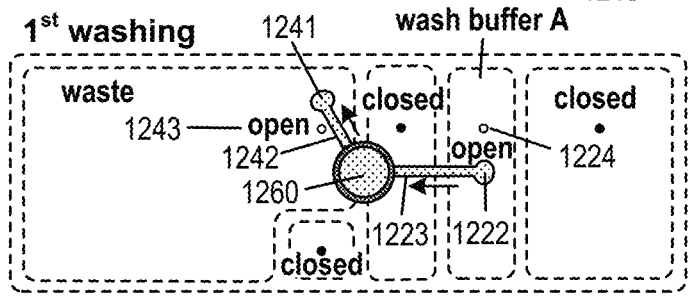

Referring to FIG. 13B, a wash step is shown. Wash buffer A compartment 1220 and waste compartment 1240 may be opened by solenoid valves connected to air-inlets or reservoir of the wash buffer A (1224, 1222) and waste (1243) compartments. All of the other air-inlets may be closed by the corresponding valves so that the wash buffer A solution only passes through microfluidic channels 1223 and 1242. Pressurized air may be applied to the wash buffer A compartment through air-inlet 1224 to initiate the flow. These channels may be located in the same microfluidic layers shown in FIG. 13A. The reservoir 1222 connected to the wash buffer A compartment in FIG. 13B may be located in the first layer and the channel 1242 on the waste side may be located in the second layer. Overlapping between these channels may be the collection area 1261 and filter 1270 as shown in FIGS. 12 and 13A to wash out unwanted materials trapped in the filter during the target cell isolation step. Afterwards, the wash buffer A (1220) and waste (1240) compartments and their corresponding air-inlets may be closed by the solenoid valves for the next step.

Figure 13C:
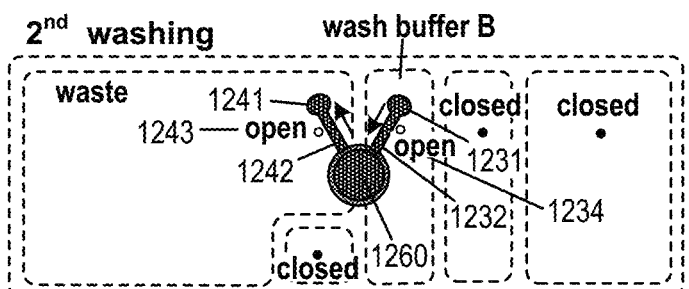

Referring to FIGS. 12 and 13C, a second wash step is shown. Wash buffer B compartment 1230 and waste compartment 1240 may be opened by solenoid valves connected to air-inlets of the wash buffer B (1234) and waste (1243) compartments. All of the other air-inlets may be closed by the corresponding valves so that the wash buffer B solution only passes through microfluidic channels 1233 and 1242. Pressurized air may be applied to the wash buffer B compartment through air-inlet 1234 to initiate the flow. These microfluidic channels may be located in the same layers as shown earlier. The channel 1233 connected to the wash buffer B compartment 1230 may be located in the first layer and the channel 1242 on the waste side may be located in the second layer. Overlapping between these channels may be the collection area 1261 and the same filter 1270 to wash out unnecessary materials in the filter unit. Afterwards, the wash buffer B and waste compartments may be closed by the solenoid valves for the next step. The waste compartment may comprise an absorbing porous paper, fabric or sponges to prevent re-flux of fluid.

Figure 13D:
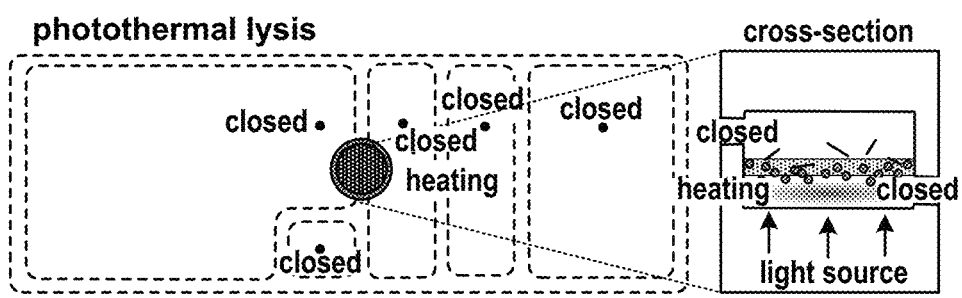

Referring to FIG. 13D, a next step as photothermal lysis of target cells is shown. During this process, all of the valves may be closed. The trapped target cells in the filter may be thermally lysed using a light source to heat the light-absorbing film located on the collection area or the light absorbing material located below the collection area. The collection area may be thermally connected to one or more light sources.

Figure 13E:
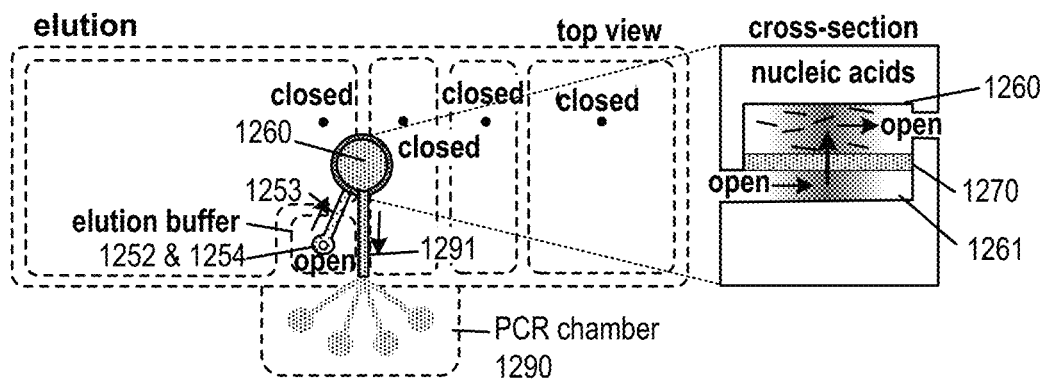
Figure 14:
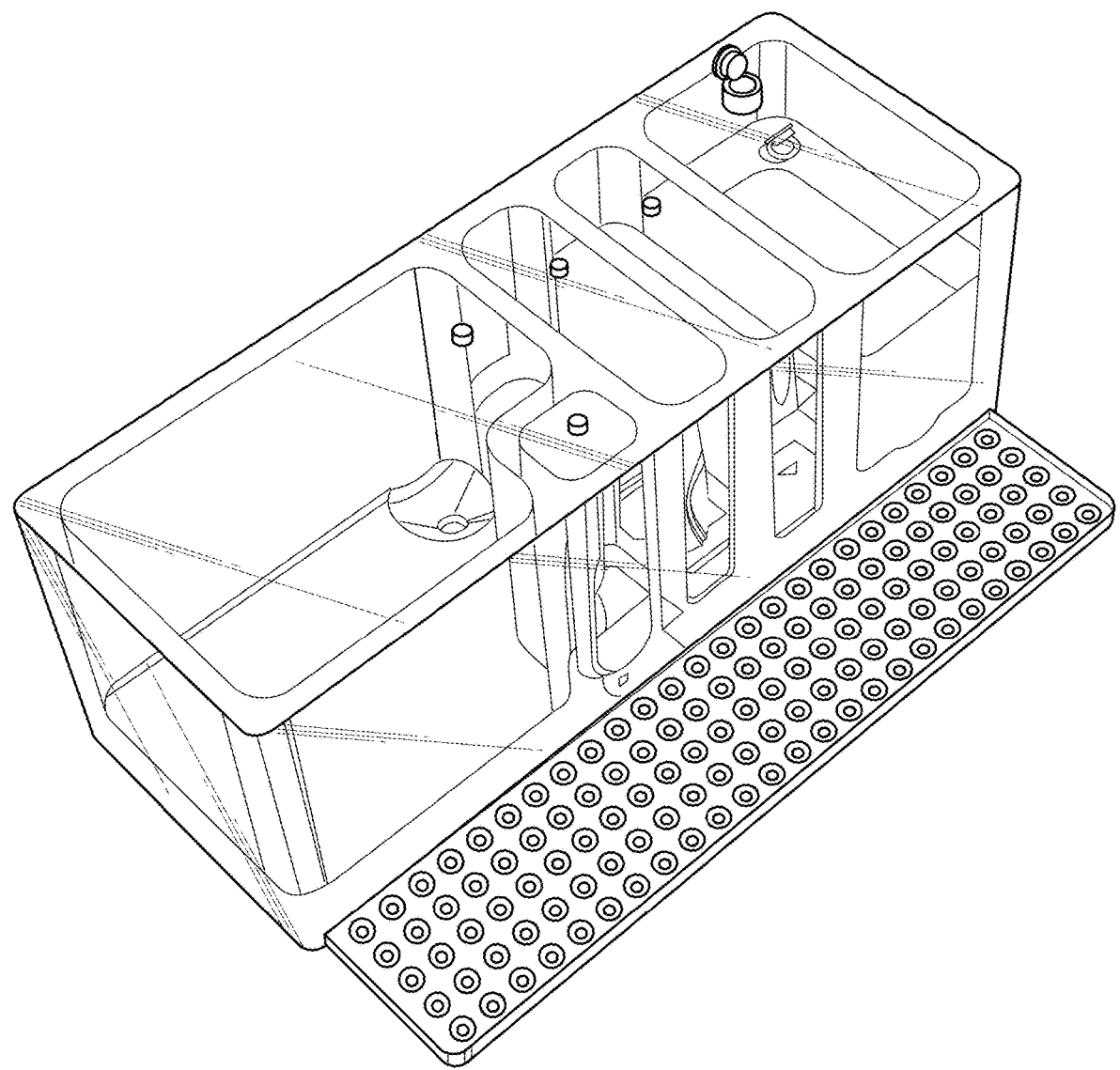
FIG. 14 is a schematic depiction of the sample preparation module with PCR reaction wells, in accordance with some embodiments.

Referring to FIGS. 12 and 13E, an elution of nucleic acids step is shown. The lysed sample may be transferred to the photonic PCR compartment. The elution step may be initiated by opening the through-holes 1251 and reservoir 1252 of the elution buffer compartment 1250 and applying pressurized air to the same compartment using air-inlet 1254. All of the other air-inlets may be closed so that the eluted sample only passes through channels 1253 (elution buffer channel) and 1291 (PCR compartment). The channel 1253 connected to the elution buffer compartment 1250 may be located in the first layer and the channel 1291 on the PCR compartment 1290 may be located in the second layer. Overlapping between these channels may be the same filter 1270 in the filter unit. Afterwards, all of the air-inlets may be closed by the solenoid valves for the PCR process. The elution compartment may have one or more electrodes placed around the compartment to change the pH of the solution by applying different voltages. In FIGS. 13A-E, the PCR unit 1290 has been shown to have four reaction wells but in some cases, the PCR unit may have more wells as described elsewhere herein as shown in FIG. 14. The sample preparation module with PCR reaction wells illustrated in FIG. 14 shares common elements with the sample preparation module with PCR reaction wells illustrated in FIG. 12 and the description provided in relation to FIG. 12 is applicable to FIG. 14 as appropriate. In FIG. 14, the number of PCR reaction wells is greater than the four PCR wells illustrated in FIGS. 12 and 13E.

The systems and methods described herein may be used to detect target cells in a biological sample. The detection limit for an assay using the methods and systems described herein may be as low as 2 copies of DNA. The detection limit may be 2 copies of DNA, 5 copies of DNA, 10 copies of DNA or 20 copies of DNA in a biological sample.

In some cases, the systems and methods herein may be used to detect target cells in a biological sample. The detection limit for an assay using the methods and systems described herein may be as low as 2 CFU/ml in a biological sample. In some cases, the detection rate is as low as 2 CFU/ml, 5, 7 CFU/ml, 10 CFU/ml, 12 CFU/ml, 15 CFU/ml, 20 CFU/ml or 25 CFU/ml in a biological sample.

Digital Processing Device

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user.

In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 15:
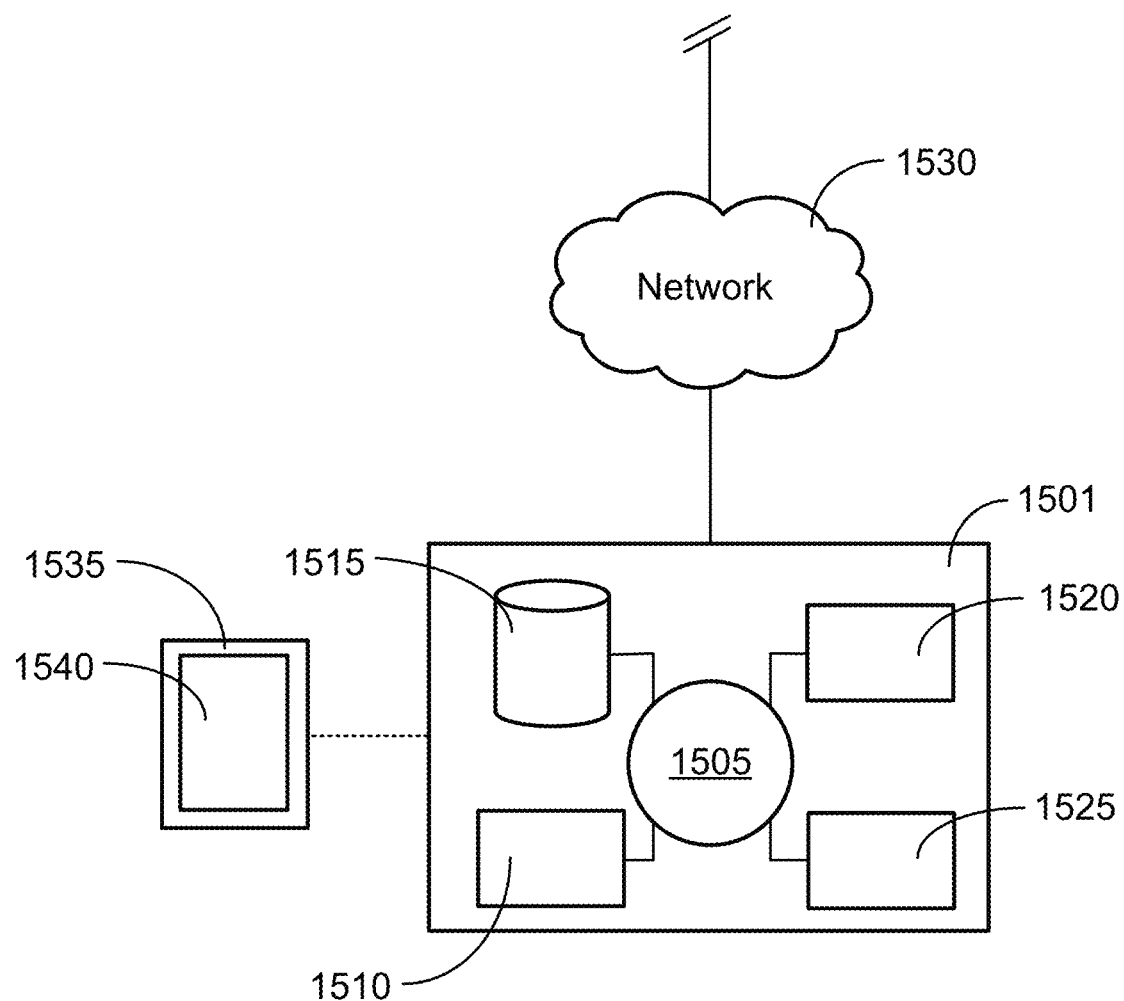
FIG. 15 shows a non-limiting example of a digital processing device; in this case, a device with one or more CPUs, a memory, a communication interface, and a display.

Referring to FIG. 15, in some embodiments, an exemplary digital processing device 1501 is programmed or otherwise configured to load samples and reagents, control temperatures in the reaction vessel, cool the reaction vessels and analyze signals from reaction vessels. The device 1501 can regulate various aspects of the present disclosure, such as, for example, increasing and decreasing the temperature of the reaction vessel using the light source(s) and the cooling channels. In this embodiment, the digital processing device 1501 includes a central processing unit (CPU, also "processor" and "computer processor" herein) 1505, which can be a single core or multi core processor, or a plurality of processors for parallel processing. The digital processing device 1501 also includes memory or memory location 1510 (e.g., random-access memory, read-only memory, flash memory), electronic storage unit 1515 (e.g., hard disk), communication interface 1520 (e.g., network adapter) for communicating with one or more other systems, and peripheral devices 1525, such as cache, other memory, data storage and/or electronic display adapters. The memory 1510, storage unit 1515, interface 1520 and peripheral devices 1525 are in communication with the CPU 1505 through a communication bus (solid lines), such as a motherboard. The storage unit 1515 can be a data storage unit (or data repository) for storing data. The digital processing device 1501 can be operatively coupled to a computer network ("network") 1530 with the aid of the communication interface 1520. The network 1530 can be the Internet, an internet and/or extranet, or an intranet and/or extranet that is in communication with the Internet. The network 1530 in some cases is a telecommunication and/or data network. The network 1530 can include one or more computer servers, which can enable distributed computing, such as cloud computing. The network 1530, in some cases with the aid of the device 1501, can implement a peer-to-peer network, which may enable devices coupled to the device 1501 to behave as a client or a server.

Continuing to refer to FIG. 15, the CPU 1505 can execute a sequence of machine-readable instructions, which can be embodied in a program or software. The instructions may be stored in a memory location, such as the memory 1510. The instructions can be directed to the CPU 1505, which can subsequently program or otherwise configure the CPU 1505 to implement methods of the present disclosure. Examples of operations performed by the CPU 1505 can include fetch, decode, execute, and write back. The CPU 1505 can be part of a circuit, such as an integrated circuit. One or more other components of the device 1501 can be included in the circuit. In some cases, the circuit is an application specific integrated circuit (ASIC) or a field programmable gate array (FPGA).

Continuing to refer to FIG. 15, the storage unit 1515 can store files, such as drivers, libraries and saved programs. The storage unit 1515 can store user data, e.g., user preferences and user programs. The digital processing device 1501 in some cases can include one or more additional data storage units that are external, such as located on a remote server that is in communication through an intranet or the Internet.

Continuing to refer to FIG. 15, the digital processing device 1501 can communicate with one or more remote computer systems through the network 1530. For instance, the device 1501 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 1501, such as, for example, on the memory 1510 or electronic storage unit 1515. The machine executable or machine readable code can be provided in the form of software. During use, the code can be executed by the processor 1505. In some cases, the code can be retrieved from the storage unit 1515 and stored on the memory 1510 for ready access by the processor 1505. In some situations, the electronic storage unit 1515 can be precluded, and machine-executable instructions are stored on memory 1510.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of information such as protocols, cycle times, temperature ranges, results, detection results and reports. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Figure 16:
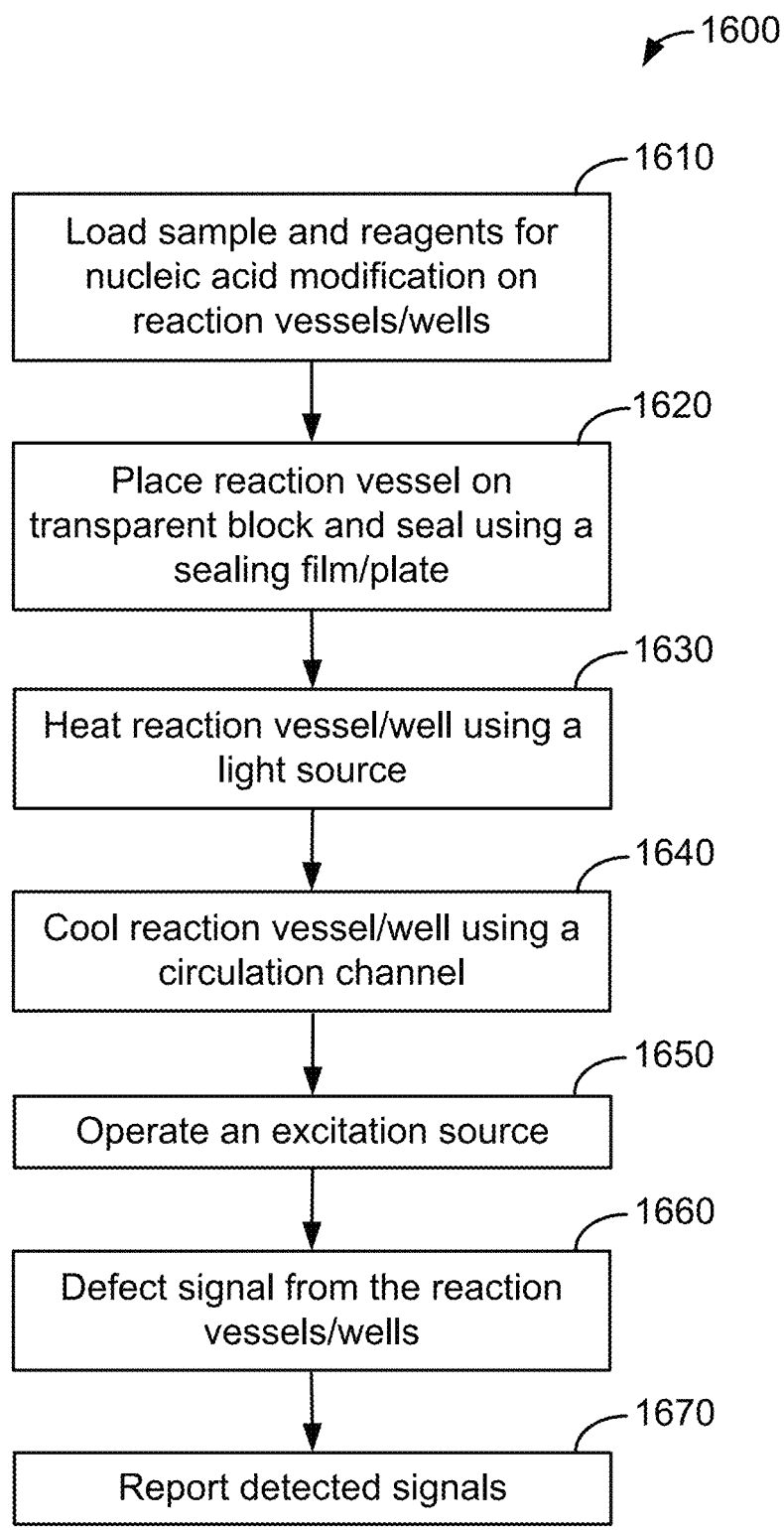
FIG. 16 shows a flowchart of a method for modifying nucleic acids and determining target nucleic acids, in accordance with some embodiments.

Referring to FIG. 16, a method 1600 for determining a target nucleic acid modification is shown. The method 1600 may use one or more of the systems described herein. In a first step 1610, samples and/or reagents required for the modification of nucleic acids may be loaded on the reaction vessel or reaction wells. In some cases, the reagents may be pre-loaded on to the wells of the reaction vessel. In a second step 1620, the reaction vessel may be placed on the transparent block. In some cases, the reaction vessel may be placed above the base with the light supports without the use of an additional transparent block. The reaction vessel may be sealed using a sealing film or a sealing plate described herein. In a third step 1630, the reaction vessel may be heated using a light source. The light source may be operated in a continuous or in a pulsed manner as described herein. The fourth step 1640, the reaction vessel may be cooled using a fluid circulation channel in the transparent block. In a fifth step 1650, an excitation source may be used to excite the fluorescent dyes integrated during the nucleic acid modification process. This step may be performed during the nucleic acid modification cycles or after the nucleic acid modification cycles. In a sixth step 1660, sensors may be used to detect the refracted light from the wells. In a seventh step 1670, the signals from the plurality of reaction wells may be reported as an output.

In some instances, a processor may be provided. The processor may be configured with instructions to perform a series of steps illustrated in FIG. 16 and others as described herein. In some instances, the processor may provide instructions for the modification of nucleic acids and detection of a target nucleic acid. A processor may be used to perform some protocols for nucleic acid modification, to pulse a light source or an excitation source. A processor may also be used to cool the reaction vessel at different time intervals.

Although the steps described above show a method of modification of nucleic acids and detection of a target nucleic acid, one of ordinary skill in the art will recognize many variations based on the teachings described herein. The steps may be completed in a different order. Steps may be added or deleted. Some of the steps may comprise sub-steps. Many of the steps may be repeated as often as necessary to detect the nucleic acid as desired. In some embodiments, a processor is configured to perform one or more steps of a method as described herein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

Example 1: Use as a Point of Care Device

Figure 17:
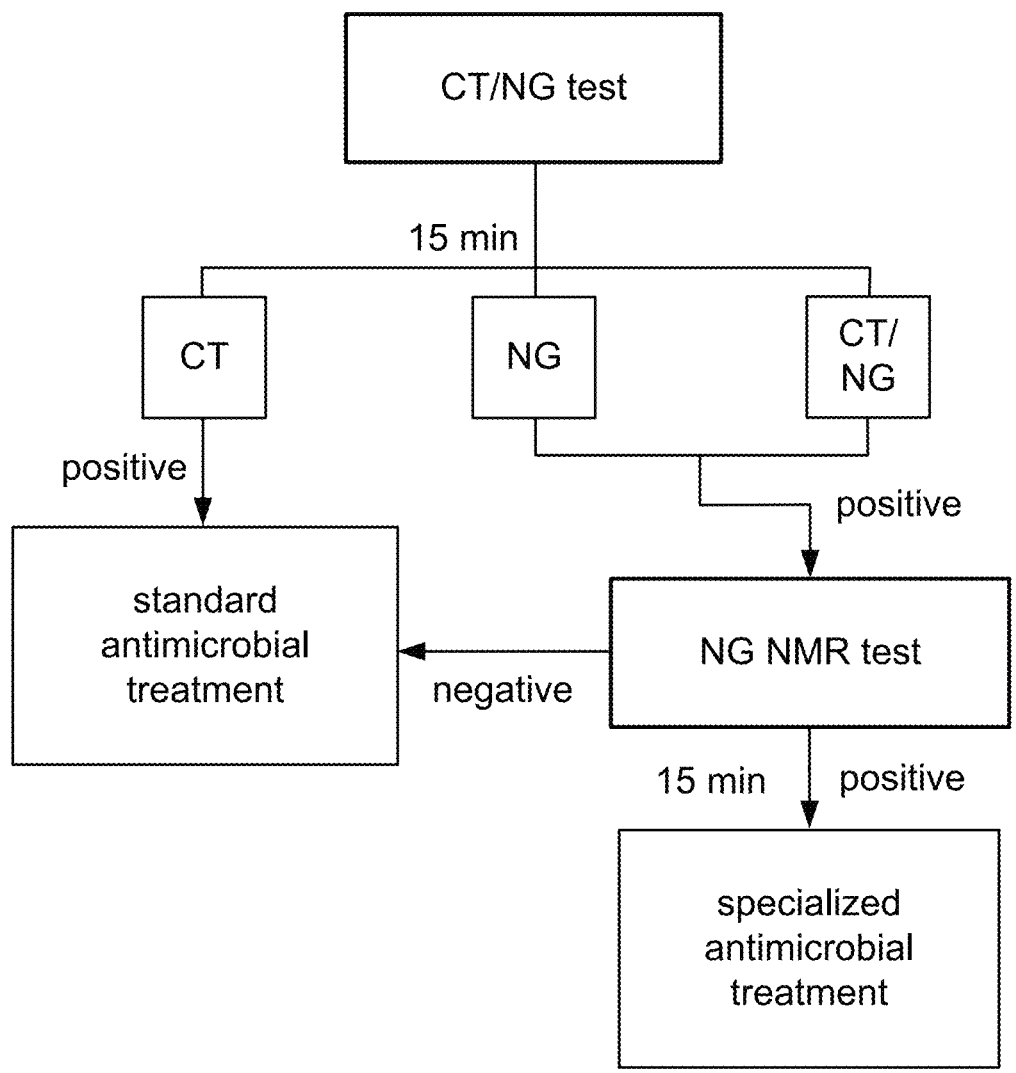
FIG. 17 shows a schematic depicting an example of using the methods and systems for detection of a target cell.

Due to the high co-infection rate of *Chlamydia trachomatis* (CT) and *Neisseria gonorrhea* (NG) and the ability of NG to mutate to a variety of gonococcal antimicrobial-resistant (AMR) strains, high-throughput detection is beneficial for diagnosing CT/NG and NG AMR. Therefore, high-throughput multiplexed PCR-based point of care testing would be beneficial. Presented in FIG. 17 is a systematic diagnostic solution for detecting CT/NG in 15 min and follow-up AMR test for NG upon positive test result in additional 15 min, delivering a fully reliable diagnostic decision within the single test. This systematic approach may include; 1) a cartridge-based sample preparation module; 2) a pneumatic pressure driven liquid handling platform; 3) a photonic PCR thermal cycler; and 4) a microfluidic array device as described previously herein for high-throughput DNA amplifications of CT/NG and gonococcal AMR. Positive results of these tests may help in generating an effective treatment plan.

Figure 18A:
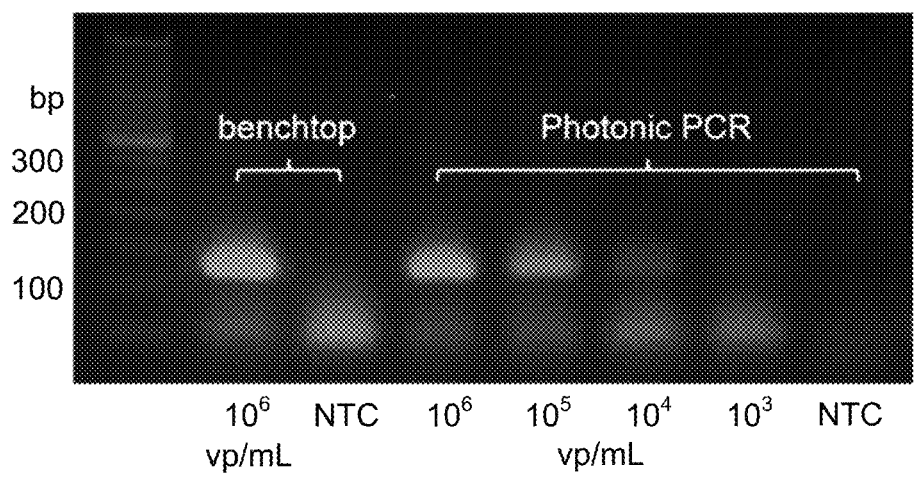
FIGS. 18A-18C show representative end-point data for detection of various gene sequences.
Figure 18B:
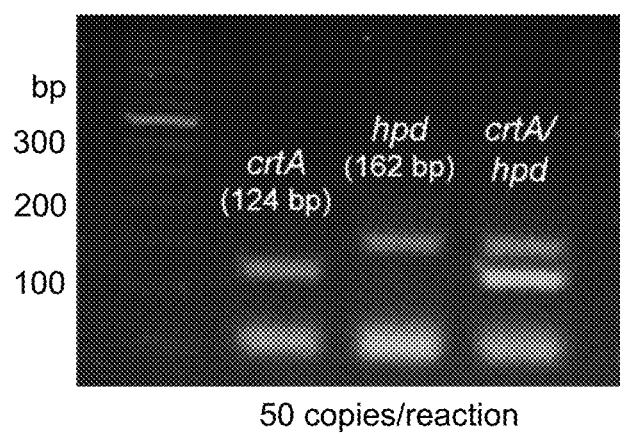
Figure 18C:
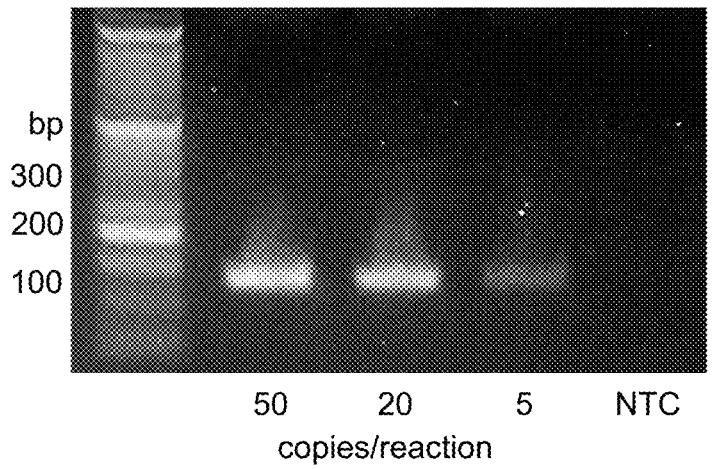

Example 2: Representative End-Point Photonic PCR Data for Various Gene Sequences FIGS. 18A-C shows the demonstration of the end-point photonic PCR for various amplifications, including DENV-1 cDNA (dengue fever), crtA (for N. meningitidis), hpd (for *Haemophilus influenzae*), and mecA (for Methicillin-resistant S. aureus). Purified nucleic acids (RNA for dengue fever converted to cDNA and DNA for crtA, hpd and mecA) were used for detection. Two-step PCR thermal cycling from 98° C. to 68° C. was employed with 40 cycles of amplification. Reaction volume of PCR was 10 µL. The amplified product was then run on a gel and compared to results from conventional PCR used as a positive control. The gel band intensity shows a clear trend as a function of template DNA concentration (FIGS. 18A and 18C). Multiplex photonic PCR is also demonstrated using crtA and hpd multiplexed reactions (FIG. 18B). It is noted that as low as 5 copies of mecA gene and $10^3$ viral particles per ml (vp/ml) were successfully amplified and confirmed by gel electrophoresis after photonic PCR amplification (FIGS. 18A and 18C).

What is claimed is:

1. A system comprising:
a polymeric fluidic device comprising one or more reaction wells;
a first support comprising a concave region;
a first light absorbing material disposed on the concave region of the first support;
a second support opposite the first support, wherein the second support comprises a convex region, wherein the first light absorbing material and the convex region of the second support define a reaction well of the one or more reaction wells;
first and second ports coupled to the one or more reaction wells;
wherein the first and second ports are configured to allow input of a fluidic sample into the one or more reaction wells;
a lyophilized reagent is pre-loaded on the one or more reaction wells; and
a light source configured to illuminate the first light absorbing material;
wherein a first portion of light illuminated onto the first light absorbing material is absorbed into the first light absorbing material; and
wherein the first portion of light absorbed into the first light absorbing material is configured to elevate a temperature of the first light absorbing material to heat the fluidic sample within the one or more reaction wells.

2. The system of claim 1 wherein:
a second light absorbing material is disposed on the convex region of the second support;
a second portion of the light illuminated onto the first light absorbing material is transmitted through the first light absorbing material and illuminates the second light absorbing material; and
at least a portion of the transmitted light illuminated onto the second light absorbing material is absorbed into the second light absorbing material; and
the light absorbed into the second light absorbing material is configured to elevate a temperature of the second light absorbing material to further heat the fluidic sample within the one or more reaction wells.

3. The system of claim 1 further comprising a first filter for emission of fluorescent dye and a second filter for elimination of light from the light source.

4. The system of claim 1 wherein the lyophilized reagent further comprises a stabilizing reagent including paraffin wax or hydrogel.

5. The system of claim 1 further comprising a fluidic valve between wells.

6. The system of claim 1 wherein the polymeric fluidic device comprises a fluid circulation channel.

7. The system of claim 6 wherein at least one of air, water, or a liquid flows through the fluid circulation channel.

8. The system of claim 1 wherein the light source comprises a pulsed light source.

9. The system of claim 8 further comprising a detector operable to detect a signal indicating nucleic acids modification during an off cycle of the pulsed light source.

10. The system of claim 1 wherein the first light absorbing material comprises one or multiple open areas.

11. A system comprising:
a sample preparation module comprising multiple compartments and a cartridge, wherein the multiple compartments comprises a sample compartment, one or more wash buffer compartments, an elution buffer compartment, and a waste compartment;
wherein the cartridge comprises:
a first microfluidic channel layer comprising a passageway connected to the sample compartment a second microfluidic channel layer comprising a first reservoir in communication with the passageway in the first microfluidic channel layer, wherein the second microfluidic channel layer comprises:
a collection area; and
a first microfluidic channel connecting the first reservoir to the collection area; and a microfluidic PCR device including photonic PCR wells in fluid communication with the collection area via a second microfluidic channel.

12. The system of claim 11 wherein the sample preparation module comprises one or more filters in a compartment at least one of the multiple compartments.

13. The system of claim 12 wherein the one or more filters comprise a first filter and a second filter, wherein the first filter and the second filter have different pore sizes.

14. The system of claim 13 wherein:
the first filter is configured to remove large debris, crystals and/or large cells from a sample; and
the second filter is configured to trap cells of interest based on the size of cells.

15. The system of claim 13 wherein the second filter comprises a layer of light absorbing material.

16. The system of claim 15 wherein the layer of light absorbing material is disposed in at least one of the multiple compartments below the second filter.

17. The system of claim 11 wherein the sample compartment comprises electrodes placed around the sample compartment to change the pH of a solution disposed in the sample compartment by applying voltage.

18. The system of claim 11 wherein the waste compartment comprises at least one of absorbing porous paper, fabric, or a sponge to prevent re-fluxes of fluid.

19. The system of claim 11 wherein the microfluidic PCR device includes a set of primers and probes to detect one or more target nucleic acids.

20. The system of claim 11 wherein the system comprises a light absorbing material including one or more open areas.

21. The system of claim 11, further comprising:
a second reservoir in fluid communication with the one or more wash buffer compartments;
a third microfluidic channel connecting the second reservoir to the collection area;
a third reservoir in fluid communication with the elution buffer compartment; and
a fourth microfluidic channel connecting the third reservoir to the collection area.

22. The system of claim 11 wherein the collection area comprises a light absorbing material.

23. The system of claim 11 wherein the collection area comprises a filter between the first microfluidic channel layer and the second microfluidic channel layer.

* * * * *